(12) United States Patent
Sotak et al.

(10) Patent No.: US 10,499,892 B2
(45) Date of Patent: Dec. 10, 2019

(54) TEMPORARY OCCLUSION BALLOON DEVICES AND METHODS FOR PREVENTING BLOOD FLOW THROUGH A VASCULAR PERFORATION

(71) Applicant: The Spectranetics Corporation, Colorado Springs, CO (US)

(72) Inventors: Ryan Michael Sotak, Colorado Springs, CO (US); Grant Foy, Colorado Springs, CO (US); Phil Aranas, Union City, CA (US); Jay Harper, Castle Rock, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 297 days.

(21) Appl. No.: 15/071,533

(22) Filed: Mar. 16, 2016

(65) Prior Publication Data
US 2017/0042519 A1 Feb. 16, 2017

Related U.S. Application Data

(60) Provisional application No. 62/203,711, filed on Aug. 11, 2015, provisional application No. 62/212,023, (Continued)

(51) Int. Cl.
*A61M 29/00* (2006.01)
*A61B 17/00* (2006.01)
(Continued)

(52) U.S. Cl.
CPC .... *A61B 17/0057* (2013.01); *A61B 17/00491* (2013.01); *A61B 17/12109* (2013.01);
(Continued)

(58) Field of Classification Search
CPC ........ A61B 17/12109; A61B 17/12113; A61B 17/12122; A61B 17/12022;
(Continued)

(56) References Cited

U.S. PATENT DOCUMENTS

| 3,834,394 A | 9/1974 | Hunter et al. |
| 4,413,989 A | 11/1983 | Schjeldahl et al. |

(Continued)

FOREIGN PATENT DOCUMENTS

| EP | 0760688 B1 | 11/2001 |
| EP | 0981387 B1 | 11/2003 |

(Continued)

OTHER PUBLICATIONS

B. Braun Interventional Systems, One Tyshak Balloon Dilation Catheter Instructions for Use, 2 pages, Publicly Available Before the Earliest Priority Date.

(Continued)

*Primary Examiner* — Melanie R Tyson

(57) ABSTRACT

A device for occluding a perforation in a blood vessel includes a catheter shaft that has a first lumen and a second lumen. The first lumen is adapted to receive at least one of a guidewire and an implanted cardiac lead, and the second lumen is adapted to receive an inflation fluid. The device further includes an inflatable balloon that is carried by the catheter shaft. The inflatable balloon is adapted to receive the inflation fluid from the second lumen. The inflatable balloon has a working length of about 65 mm to about 80 mm and an inflated diameter of about 20 mm to about 25 mm.

17 Claims, 20 Drawing Sheets

Related U.S. Application Data filed on Aug. 31, 2015, provisional application No. 62/212,025, filed on Aug. 31, 2015, provisional application No. 62/233,869, filed on Sep. 28, 2015, provisional application No. 62/234,376, filed on Sep. 29, 2015, provisional application No. 62/260,945, filed on Nov. 30, 2015, provisional application No. 62/297,785, filed on Feb. 19, 2016.

(51) Int. Cl.
  *A61B 17/12* (2006.01)
  *A61M 25/10* (2013.01)
  *A61B 90/00* (2016.01)

(52) U.S. Cl.
  CPC ..... *A61B 17/1204* (2013.01); *A61B 17/12136* (2013.01); *A61B 2017/0065* (2013.01); *A61B 2017/00292* (2013.01); *A61B 2017/00557* (2013.01); *A61B 2017/00597* (2013.01); *A61B 2017/00623* (2013.01); *A61B 2017/00659* (2013.01); *A61B 2017/00676* (2013.01); *A61B 2090/3966* (2016.02); *A61M 2025/105* (2013.01); *A61M 2025/1079* (2013.01)

(58) Field of Classification Search
  CPC .......... A61B 17/0057; A61B 17/12136; A61B 2017/00659; A61B 2017/0065; A61B 2017/00676; A61B 2017/00623; A61B 2017/00292; A61M 25/10
  USPC .................................................. 606/194, 213
  See application file for complete search history.

(56) References Cited

U.S. PATENT DOCUMENTS

| | | | |
|---|---|---|---|
| 4,545,390 | A | 10/1985 | Leary |
| 4,689,041 | A | 8/1987 | Corday et al. |
| 4,836,204 | A | 6/1989 | Landymore et al. |
| 5,273,536 | A | 12/1993 | Savas |
| 5,304,121 | A | 4/1994 | Sahatjian |
| 5,338,298 | A | 8/1994 | McIntyre |
| 5,358,487 | A | 10/1994 | Miller |
| 5,383,856 | A | 1/1995 | Bersin |
| 5,417,689 | A | 5/1995 | Fine |
| 5,439,445 | A | 8/1995 | Kontos |
| 5,447,497 | A | 9/1995 | Sogard et al. |
| 5,470,313 | A | 11/1995 | Crocker et al. |
| 5,496,311 | A | 3/1996 | Abele et al. |
| 5,540,679 | A | 7/1996 | Fram et al. |
| 5,599,306 | A | 2/1997 | Klein et al. |
| 5,613,948 | A | 3/1997 | Avellanet |
| 5,759,170 | A | 6/1998 | Peters |
| 5,765,568 | A | 6/1998 | Sweezer et al. |
| 5,766,151 | A | 6/1998 | Valley et al. |
| 5,795,325 | A * | 8/1998 | Valley .............. A61B 17/12022 604/103.1 |
| 5,795,331 | A | 8/1998 | Cragg et al. |
| 5,797,878 | A | 8/1998 | Bleam |
| 5,800,393 | A | 9/1998 | Sahota |
| 5,820,595 | A | 10/1998 | Parodi |
| 5,823,996 | A | 10/1998 | Sparks |
| 5,843,027 | A | 12/1998 | Stone et al. |
| 5,843,116 | A | 12/1998 | Crocker et al. |
| 5,865,787 | A | 2/1999 | Shapland et al. |
| 5,885,244 | A | 3/1999 | Leone et al. |
| 5,985,307 | A | 11/1999 | Hanson et al. |
| 6,048,333 | A | 4/2000 | Lennox et al. |
| 6,071,271 | A | 6/2000 | Baker et al. |
| 6,159,197 | A | 12/2000 | Heuser |
| 6,176,821 | B1 | 1/2001 | Crocker et al. |
| 6,221,043 | B1 | 4/2001 | Fischell et al. |
| 6,251,094 | B1 | 6/2001 | Bleam |
| 6,258,019 | B1 | 7/2001 | Verin et al. |
| 6,293,924 | B1 | 9/2001 | Bagaoisan et al. |
| 6,315,757 | B1 | 11/2001 | Chee et al. |
| 6,346,092 | B1 | 2/2002 | Leschinsky |
| 6,458,069 | B1 | 10/2002 | Tam et al. |
| 6,461,327 | B1 | 10/2002 | Addis et al. |
| 6,485,500 | B1 | 11/2002 | Kokish et al. |
| 6,491,663 | B1 | 12/2002 | Lemelson |
| 6,540,721 | B1 * | 4/2003 | Voyles .................. A61B 17/22 604/103.1 |
| 6,572,633 | B1 | 6/2003 | Loffler et al. |
| 6,579,847 | B1 | 6/2003 | Unger |
| 6,613,066 | B1 | 9/2003 | Fukaya et al. |
| 6,616,629 | B1 | 9/2003 | Verin et al. |
| 6,623,504 | B2 | 9/2003 | Vrba et al. |
| 6,626,861 | B1 | 9/2003 | Hart et al. |
| 6,629,952 | B1 | 10/2003 | Chien et al. |
| 6,645,167 | B1 | 11/2003 | Whalen, II et al. |
| 6,652,441 | B2 | 11/2003 | Weinberger et al. |
| 6,652,485 | B1 | 11/2003 | Gaudoin et al. |
| 6,656,153 | B1 | 12/2003 | Sakai et al. |
| 6,663,614 | B1 | 12/2003 | Carter |
| 6,679,900 | B2 | 1/2004 | Kieturakis et al. |
| 6,682,545 | B1 | 1/2004 | Kester |
| 6,699,170 | B1 | 3/2004 | Crocker et al. |
| 6,706,010 | B1 | 3/2004 | Miki et al. |
| 6,723,070 | B1 | 4/2004 | Arai et al. |
| 6,743,208 | B1 | 6/2004 | Coyle |
| 6,743,227 | B2 | 6/2004 | Seraj et al. |
| 6,875,209 | B2 | 4/2005 | Zvuloni et al. |
| 6,902,571 | B2 * | 6/2005 | Owens ................ A61M 25/104 604/103.06 |
| 6,936,057 | B1 | 8/2005 | Nobles |
| 6,955,658 | B2 | 10/2005 | Murray et al. |
| 6,960,186 | B1 | 11/2005 | Fukaya et al. |
| 7,137,395 | B2 | 11/2006 | Fried et al. |
| 7,169,140 | B1 | 1/2007 | Kume |
| 7,232,452 | B2 | 6/2007 | Adams et al. |
| 7,247,147 | B2 | 7/2007 | Nishide et al. |
| 7,306,575 | B2 | 12/2007 | Barbut et al. |
| 7,322,959 | B2 | 1/2008 | Warnack et al. |
| 7,402,172 | B2 | 7/2008 | Chin et al. |
| 7,491,188 | B2 | 2/2009 | Holman et al. |
| 7,645,290 | B2 | 1/2010 | Lucas |
| 7,674,240 | B2 | 3/2010 | Webler et al. |
| 7,722,568 | B2 | 5/2010 | Lenker et al. |
| 7,727,228 | B2 | 6/2010 | Abboud et al. |
| 7,862,575 | B2 | 1/2011 | Tal |
| 7,862,577 | B2 | 1/2011 | Gray et al. |
| 7,909,794 | B2 | 3/2011 | Briscoe et al. |
| 7,931,663 | B2 | 4/2011 | Farnan et al. |
| 7,942,850 | B2 | 5/2011 | Levit et al. |
| 7,967,836 | B2 | 6/2011 | Warnack et al. |
| 8,021,386 | B2 | 9/2011 | Davidson et al. |
| 8,066,667 | B2 | 11/2011 | Hayman et al. |
| 8,172,783 | B1 | 5/2012 | Ray |
| 8,177,779 | B2 | 5/2012 | Joye et al. |
| 8,182,446 | B2 | 5/2012 | Schaeffer et al. |
| 8,221,342 | B2 | 7/2012 | Mesallum |
| 8,231,617 | B2 | 7/2012 | Satake |
| 8,235,941 | B2 | 8/2012 | Hayman et al. |
| 8,292,913 | B2 | 10/2012 | Warnack et al. |
| 8,323,307 | B2 | 12/2012 | Hardert |
| 8,348,890 | B2 | 1/2013 | Gerrans et al. |
| 8,372,034 | B2 | 2/2013 | Levit et al. |
| 8,382,787 | B2 | 2/2013 | Burton et al. |
| 8,414,611 | B2 | 4/2013 | Chalekian |
| 8,419,714 | B2 | 4/2013 | Webler et al. |
| 8,486,046 | B2 | 7/2013 | Hayman et al. |
| 8,518,105 | B2 | 8/2013 | Hossainy et al. |
| 8,563,510 | B2 | 10/2013 | Hakimimehr et al. |
| 8,574,225 | B2 | 11/2013 | Reynolds |
| 8,667,838 | B2 | 3/2014 | Hoem et al. |
| 8,708,996 | B2 | 4/2014 | Consigny et al. |
| 8,740,961 | B2 | 6/2014 | Fulton et al. |
| 8,784,602 | B2 | 7/2014 | Schaeffer et al. |
| 8,801,662 | B2 | 8/2014 | Doshi et al. |
| 8,852,146 | B2 | 10/2014 | Horn et al. |
| 8,864,705 | B2 | 10/2014 | Nishigishi |
| 8,936,568 | B2 | 1/2015 | Webler et al. |

(56) References Cited

U.S. PATENT DOCUMENTS

| | | | |
|---|---|---|---|
| 8,974,409 B2 | 3/2015 | Hayman et al. | |
| 8,986,339 B2 | 3/2015 | Warnack et al. | |
| 9,044,580 B2 | 6/2015 | Freyman et al. | |
| 9,173,817 B2 | 11/2015 | Sharma et al. | |
| 9,358,042 B2 | 6/2016 | Magee | |
| 9,504,807 B2 | 11/2016 | Drasler et al. | |
| 9,522,215 B2 | 12/2016 | Rago et al. | |
| 9,579,449 B2 | 2/2017 | Sharma et al. | |
| 2002/0010411 A1 | 1/2002 | Macoviak et al. | |
| 2002/0026210 A1 | 2/2002 | Abdel-Gawwad | |
| 2002/0133217 A1 | 9/2002 | Sirhan et al. | |
| 2003/0004462 A1 | 1/2003 | Halpin | |
| 2003/0050600 A1 | 3/2003 | Ressemann et al. | |
| 2003/0050660 A1* | 3/2003 | Hackett | A61M 25/0021 606/194 |
| 2003/0163154 A1 | 8/2003 | Miyata et al. | |
| 2003/0199914 A1 | 10/2003 | Diaz | |
| 2003/0220666 A1 | 11/2003 | Mirigian et al. | |
| 2004/0006305 A1 | 1/2004 | Hebert et al. | |
| 2004/0122362 A1 | 6/2004 | Houser et al. | |
| 2004/0249243 A1 | 12/2004 | Kleiner | |
| 2004/0267196 A1 | 12/2004 | Miki et al. | |
| 2005/0015047 A1 | 1/2005 | Shah | |
| 2005/0033263 A1 | 2/2005 | Gottlieb et al. | |
| 2005/0075711 A1 | 4/2005 | Neary | |
| 2005/0209674 A1 | 9/2005 | Kutscher et al. | |
| 2006/0095065 A1 | 5/2006 | Tanimura et al. | |
| 2006/0167442 A1 | 7/2006 | Hebert et al. | |
| 2006/0173298 A1 | 8/2006 | Tucker | |
| 2006/0258981 A1 | 11/2006 | Eidenschink | |
| 2007/0203453 A1 | 8/2007 | Mori et al. | |
| 2008/0287907 A1* | 11/2008 | Gregory | A61F 2/04 604/500 |
| 2009/0054922 A1 | 2/2009 | Broker | |
| 2009/0076447 A1 | 3/2009 | Casas et al. | |
| 2009/0105686 A1 | 4/2009 | Snow et al. | |
| 2009/0131785 A1 | 5/2009 | Lee et al. | |
| 2009/0192452 A1 | 7/2009 | Sasajima et al. | |
| 2009/0306700 A1 | 12/2009 | Miyata et al. | |
| 2010/0004623 A1 | 1/2010 | Hamilton et al. | |
| 2010/0016833 A1 | 1/2010 | Ogle et al. | |
| 2010/0185220 A1 | 7/2010 | Naghavi et al. | |
| 2010/0324648 A1 | 12/2010 | Scheller et al. | |
| 2011/0071498 A1 | 3/2011 | Hakimimehr et al. | |
| 2011/0082465 A1 | 4/2011 | Verma | |
| 2011/0190727 A1 | 8/2011 | Edmunds et al. | |
| 2011/0190867 A1 | 8/2011 | Vonderwalde et al. | |
| 2011/0202016 A1 | 8/2011 | Zugates et al. | |
| 2012/0040137 A1 | 2/2012 | Palasis et al. | |
| 2012/0107439 A1 | 5/2012 | Sharma et al. | |
| 2012/0109177 A1 | 5/2012 | Ulmer | |
| 2012/0157987 A1 | 6/2012 | Steinke et al. | |
| 2012/0265287 A1 | 10/2012 | Sharma et al. | |
| 2012/0310210 A1 | 12/2012 | Campbell et al. | |
| 2013/0073025 A1 | 3/2013 | Kassab | |
| 2013/0090679 A1 | 4/2013 | Hoem et al. | |
| 2013/0165925 A1 | 6/2013 | Mathur et al. | |
| 2013/0172923 A1 | 7/2013 | Webler et al. | |
| 2013/0211381 A1 | 8/2013 | Feld | |
| 2013/0310687 A1 | 11/2013 | Kenji Takizawa et al. | |
| 2013/0317418 A1 | 11/2013 | Freyman et al. | |
| 2014/0018732 A1 | 1/2014 | Bagaoisan et al. | |
| 2014/0094893 A1 | 4/2014 | Gerber | |
| 2014/0100646 A1 | 4/2014 | Hassan et al. | |
| 2014/0180248 A1 | 6/2014 | Salik | |
| 2014/0228745 A1 | 8/2014 | Sharma et al. | |
| 2014/0249475 A1 | 9/2014 | Pacetti | |
| 2014/0257181 A1 | 9/2014 | Speck | |
| 2014/0257266 A1 | 9/2014 | Kasprzyk et al. | |
| 2014/0276135 A1 | 9/2014 | Agah et al. | |
| 2014/0277399 A1 | 9/2014 | Pacetti et al. | |
| 2014/0316367 A1 | 10/2014 | Zugates et al. | |
| 2015/0012031 A1 | 1/2015 | Rago et al. | |
| 2015/0032087 A1 | 1/2015 | Shibata et al. | |
| 2015/0051634 A1 | 2/2015 | Kravik et al. | |
| 2015/0080875 A1 | 3/2015 | Kasprzyk et al. | |
| 2015/0112256 A1 | 4/2015 | Byrne et al. | |
| 2015/0165171 A1 | 6/2015 | Warnack et al. | |
| 2015/0223819 A1 | 8/2015 | Rago et al. | |
| 2015/0224235 A1 | 8/2015 | Sharma et al. | |
| 2016/0051264 A1 | 2/2016 | Freyman et al. | |
| 2016/0082144 A1 | 3/2016 | Freyman et al. | |
| 2016/0114125 A1 | 4/2016 | Di Caprio et al. | |
| 2016/0278783 A1 | 9/2016 | Magee | |
| 2016/0279302 A1 | 9/2016 | Sharma et al. | |

FOREIGN PATENT DOCUMENTS

| | | |
|---|---|---|
| EP | 0853957 B1 | 6/2004 |
| EP | 1129737 B1 | 7/2005 |
| EP | 1051990 B1 | 10/2008 |
| EP | 2002779 A2 | 3/2009 |
| EP | 1879652 B1 | 6/2012 |
| EP | 1802368 B1 | 7/2013 |
| WO | 1994002195 A1 | 2/1994 |
| WO | 1998050101 A1 | 11/1998 |
| WO | 1999002202 A2 | 1/1999 |
| WO | 2004096339 A1 | 11/2004 |
| WO | 2009154720 A1 | 12/2009 |
| WO | 2010026578 A1 | 3/2010 |
| WO | 2010048729 A1 | 5/2010 |
| WO | 2010078875 A1 | 7/2010 |
| WO | 2012015623 A1 | 2/2012 |
| WO | 2012027138 A1 | 3/2012 |
| WO | 2012078612 A2 | 6/2012 |
| WO | 2014004160 A1 | 1/2014 |
| WO | 2014102611 A2 | 7/2014 |
| WO | 2014152742 A2 | 9/2014 |
| WO | 2014158687 A1 | 10/2014 |
| WO | 2015021375 A1 | 2/2015 |

OTHER PUBLICATIONS

B. Braun Interventional Systems, Z-MED II Balloon Dilation Catheter Instructions for Use, 2 pages, Publicly Available Before the Earliest Priority Date.
Bard Peripheral Vascular, Atlas PTA Dilation Catheter, 4 pages, Publicly Available Before the Earliest Priority Date.
Boston Scientific, Equalizer Occlusion Balloon Catheter Directions for Use, 6 pages, Publicly Available Before the Earliest Priority Date.
Cook Medical, Coda and Coda LP Balloon Catheters Instructions for Use, 36 pages, Publicly Available Before the Earliest Priority Date.
Cordis, Maxi LD Brochure, 2 pages, Publicly Available Before the Earliest Priority Date.
Dispomedica, Occlusion Catheter, 1 page, Publicly Available Before the Earliest Priority Date.
Edwards Lifesciences, Fogarty Occlusion Catheters—Temporary Vessel Occlusion, 2 pages, Publicly Available Before the Earliest Priority Date.
Gore, Q50 Plus Stent Graft Balloon Catheter, http://www.goremedical.com/q50/, Publicly Available Before the Earliest Priority Date.
International Preliminary Report on Patentablity issued in PCT/US2014/019274, dated Sep. 24, 2015, 10 pages.
International Search Report and Written Opinion issued for PCT/US2014/019274 dated Jun. 3, 2014, 14 pages.
ISOMed, Occlusion Catheter Single Lumen, http://www.fbmedical.fr/en/occlusion-catheter, Publicly Available Before the Earliest Priority Date.
LeMaitre Vascular, Distal Perfusion Catheter Instructions for Use, 4 pages, Publicly Available Before the Earliest Priority Date.
LeMaitre Vascular, LeMaitre Aortic Occlusion Catheter Instructions for Use, 4 pages, Publicly Available Before the Earliest Priority Date.
Medtronic, Reliant Stent Graft Balloon Catheter, 2 pages, Publicly Available Before the Earliest Priority Date.
SentreHeart, Product Catalog, 6 pages, Publicly Available Before the Earliest Priority Date.

(56) References Cited

OTHER PUBLICATIONS

International Search Report and Written Opinion issued in PCT/US2016/046489, dated Nov. 10, 2016, 12 pages.

* cited by examiner

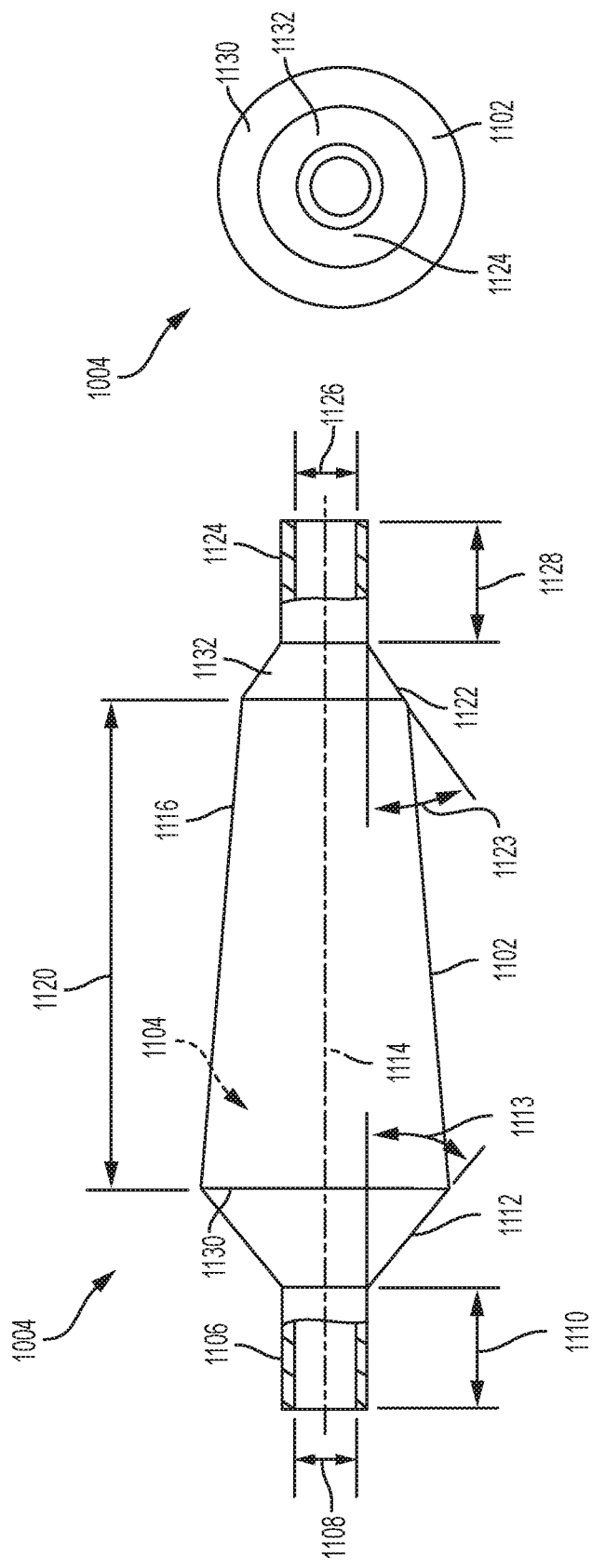

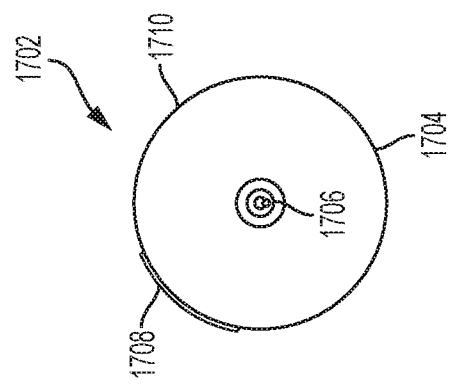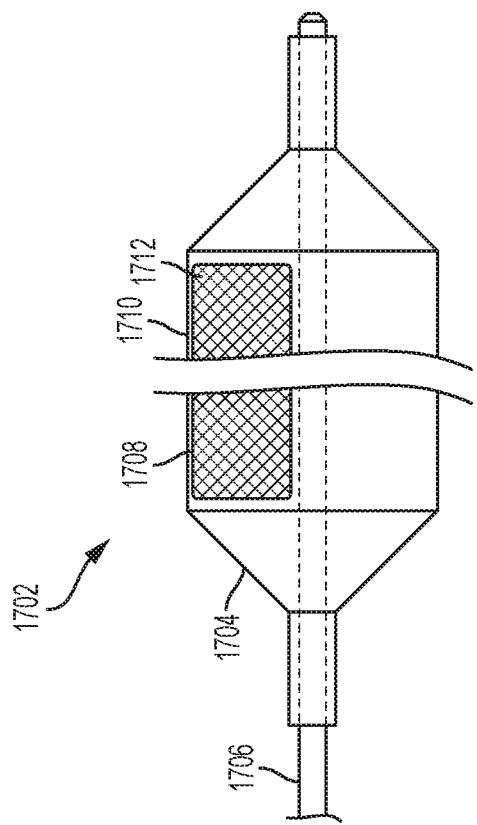
FIG. 17B
FIG. 17A

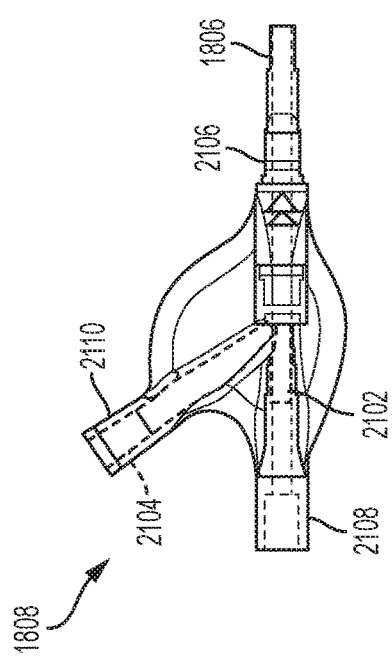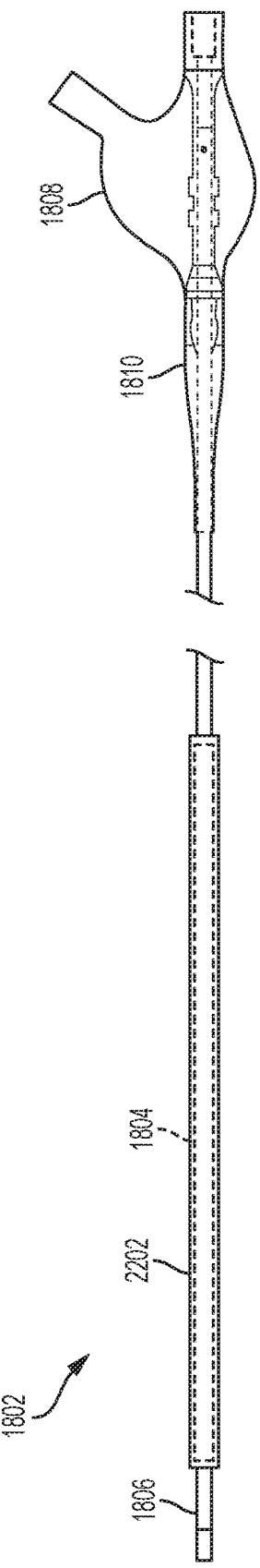
FIG. 21
FIG. 22

TEMPORARY OCCLUSION BALLOON DEVICES AND METHODS FOR PREVENTING BLOOD FLOW THROUGH A VASCULAR PERFORATION

CROSS REFERENCE TO RELATED APPLICATION

The present application is related to commonly owned U.S. Provisional Application Ser. No. 62/203,711, filed Aug. 11, 2015, entitled "TEMPORARY OCCLUSION BALLOON DEVICES AND METHODS FOR PREVENTING BLOOD FLOW THROUGH A VASCULAR PERFORATION," commonly owned U.S. Provisional Application Ser. No. 62/212,023, filed Aug. 31, 2015, entitled "TEMPORARY OCCLUSION BALLOON DEVICES AND METHODS FOR PREVENTING BLOOD FLOW THROUGH A VASCULAR PERFORATION," commonly owned U.S. Provisional Application Ser. No. 62/212,025, filed Aug. 31, 2015, entitled "TEMPORARY OCCLUSION BALLOON DEVICES AND METHODS FOR PREVENTING BLOOD FLOW THROUGH A VASCULAR PERFORATION," commonly owned U.S. Provisional Application Ser. No. 62/233,869, filed Sep. 28, 2015, entitled "TEMPORARY OCCLUSION BALLOON DEVICES AND HEMOSTATIC COMPOSITIONS FOR PREVENTING BLOOD FLOW THROUGH A VASCULAR PERFORATION," commonly owned U.S. Provisional Application Ser. No. 62/234,376, filed Sep. 29, 2015, entitled "TEMPORARY OCCLUSION BALLOON DEVICES AND METHODS FOR PREVENTING BLOOD FLOW THROUGH A VASCULAR PERFORATION," and commonly owned U.S. Provisional Application Ser. No. 62/260,945, filed Nov. 30, 2015, entitled "TEMPORARY OCCLUSION BALLOON DEVICES AND METHODS FOR PREVENTING BLOOD FLOW THROUGH A VASCULAR PERFORATION," and commonly owned U.S. Provisional Application Ser. No. 62/297,785, filed Feb. 19, 2016, entitled "TEMPORARY OCCLUSION BALLOON DEVICES AND METHODS FOR PREVENTING BLOOD FLOW THROUGH A VASCULAR PERFORATION," which are hereby incorporated herein by reference in their entireties for all that they teach and for all purposes.

FIELD OF THE DISCLOSURE

The present disclosure relates generally to medical occlusion balloon devices and methods. In particular, the present disclosure provides temporary occlusion balloon devices and methods for preventing blood flow through vascular perforations formed during cardiac lead removal procedures.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat faster. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached to the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, and lead malfunction.

Removal or extraction of the lead may be difficult. As mentioned above, the body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature.

A variety of tools have been developed to make lead extraction safer and more successful. Current lead extraction techniques include mechanical traction, mechanical devices, and laser devices. Mechanical traction may be accomplished by inserting a locking stylet into the hollow portion of the lead and then pulling the lead to remove it. An example of such a lead locking device is described and illustrated in U.S. Pat. No. 6,167,315 to Coe et al., which is incorporated herein by reference in its entirety for all that it teaches and for all purposes.

A mechanical device to extract leads includes a flexible tube called a sheath that passes over the lead and/or the surrounding tissue. The sheath typically may include a cutting blade, such that upon advancement, the cutting blade and sheath cooperate to separate the scar tissue from other scar tissue including the scar tissue surrounding the lead. In some cases, the cutting blade and sheath may also separate the tissue itself from the lead. Once the lead is separated from the surrounding tissue and/or the surrounding tissue is separated from the remaining scar tissue, the lead may be inserted into a hollow lumen of the sheath for removal and/or be removed from the patient's vasculature using some other mechanical devices, such as the mechanical traction device previously described in U.S. Pat. No. 8,961,551 to Taylor, which is hereby incorporated herein by reference in its entirety for all that it teaches and for all purposes. An example of such a such device and a method used to extract leads is described and illustrated in U.S. Pat. No. 5,651,781 to Grace, which is incorporated herein by reference in its entirety for all that it teaches and for all purposes.

Examples of a laser catheter assembly or laser sheaths that may be used for removing a surgically implanted lead is a coronary laser atherectomy catheter by the Spectranetics Corporation under the trade names SLSII™ and Glide-Light™. At the distal end, such catheters include multiple fiber optic laser emitters that surround a lumen. As the fiber optic laser emitters cut the tissue surrounding the lead, the sheath slides over the lead and surrounding tissue, which enter the lumen.

Lead extraction is generally a very safe procedure. However, as with any invasive procedure, there are potential risks. For example, while using any of the tools discussed above to remove a lead, the tool may accidentally pierce, cut, or perforate the vein or artery through which the tool is traveling, thereby allowing blood to escape the patient's vascular system. The rate at which blood escapes may be high if the accidental opening is created close to the patient's heart. Accordingly, a clinician must address the situation quickly to mitigate the amount of blood that escapes from the patient, thereby minimizing potential long-term harm to the patient.

SUMMARY

These and other needs are addressed by the various aspects, embodiments, and configurations of the present disclosure. In some embodiments, a device for occluding a perforation in a blood vessel includes a catheter shaft that has a first lumen and a second lumen. The first lumen is adapted to receive at least one of a guidewire and an implanted cardiac lead, and the second lumen is adapted to receive an inflation fluid. The second lumen may include a cross-sectional area at a location along a length of the catheter shaft between 0.65 mm$^2$ and 1.90 mm$^2$. The device further includes an inflatable balloon that is carried by the catheter shaft. The inflatable balloon is adapted to receive the inflation fluid from the second lumen. The inflatable balloon has a working length of about 65 mm to about 80 mm and an inflated diameter of about 20 mm to about 25 mm. The device may also include cross-sectional area within the second lumen that includes a crescent shape, and the cross-sectional area of the second lumen may be about 1 mm$^2$, the radius of the crescent-like cross-sectional shape may have a radius of about between 0.50 mm to 1.50 mm, such as about 1 mm.

In some embodiments, a device for occluding a perforation in a blood vessel includes an inflatable balloon coated with a hemostatic composition to reduce the rate of blood flow loss and allow more time for planning and initiating surgical repair of the perforation. The hemostatic composition can include one or more hemostatic blood clotting agents, as well as one or more adjuvants and/or excipients.

A device according to paragraph [0012], wherein the inflatable balloon includes polyurethane.

A device according to any of paragraphs [0012]-[0014], wherein the inflatable balloon includes a proximal tapered portion, a distal tapered portion, and a working portion disposed between the proximal tapered portion and the distal tapered portion, the working portion having the inflated diameter of about 20 mm to about 25 mm.

A device according to any of paragraphs [0012]-[0015], wherein the first lumen and the second lumen are non-concentrically disposed within the catheter shaft.

A device according to any of paragraphs [0012]-[0016], further including at least one radiopaque marker carried by the catheter shaft.

A device according to any of paragraphs [0012]-[0017], wherein at least one radiopaque marker includes a band extending around a circumference of the catheter shaft.

A device according to any of paragraphs [0012]-[0018], wherein at least one radiopaque marker includes at least a first radiopaque marker and a second radiopaque marker.

A device according to any of paragraphs [0012]-[0019], wherein at least one radiopaque marker further includes at least a third radiopaque marker.

A device according to any of paragraphs [0012]-[0020], wherein the hemostatic composition includes a fibrin-based clotting agent that promotes blood clotting and wound healing (e.g., fibrin sealant).

A device according to any of paragraphs [0012]-[0021], wherein the hemostatic composition includes one or more clotting agents that promotes blood clotting and wound healing, and a coating agent to prevent premature loss of the hemostatic composition while positioning the balloon adjacent to the perforation.

A device according to any of paragraphs [0012]-[0022], wherein the inflatable balloon includes a proximal portion, a distal portion, and an intermediate portion disposed between the proximal and distal portions, wherein the first, second, and third radiopaque markers are carried within the inflatable balloon, and wherein the first radiopaque marker is axially aligned with the proximal portion, the second radiopaque marker is axially aligned with the intermediate portion, and the third radiopaque marker is axially aligned with the distal portion.

A device according to any of paragraphs [0012]-[0023], wherein the inflatable balloon includes a proximal neck, a proximal tapered portion, a working portion, a distal tapered portion and a distal neck, wherein the first, second, and third radiopaque markers are carried within the inflatable balloon, and wherein the first radiopaque marker is axially aligned with an intersection of the proximal neck and the proximal tapered portion, wherein the second radiopaque marker is axially aligned with the intersection of the proximal tapered portion and the working portion, and the third radiopaque marker is axially aligned with the intersection of the working portion and the distal tapered portion.

A device according to any of paragraphs [0012]-[0024], further comprising a third lumen being adapted to facilitate passage of blood from a first end to a second end of the inflatable balloon.

A device according to any of paragraphs [0012]-[0025], wherein the catheter shaft includes the third lumen.

A device according to any of paragraphs [0012]-[0026], further comprising an occlusion patch detachably carried by the inflatable balloon, the occlusion patch being deployable from the inflatable balloon to occlude the perforation.

A device according to any of paragraphs [0012]-[0027], wherein the occlusion patch includes at least one adhesive adapted to maintain a position of the occlusion patch within the blood vessel.

A device according to any of paragraphs [0012]-[0028], wherein the at least one adhesive is adapted to be activated by application of at least one of heat, pH, and light.

A device according to any of paragraphs [0012]-[0029], wherein the occlusion patch includes a scaffold structure adapted to facilitate tissue growth therein.

A device according to any of paragraphs [0012]-[0030], wherein the occlusion patch includes stem cells to facilitate bioabsorption of the occlusion patch.

A device according to any of paragraphs [0012]-[0031], wherein the occlusion patch includes at least one hormonal agent adapted to promote wound healing.

In some embodiments, a device for occluding a perforation in a blood vessel includes a catheter shaft that has a first lumen and a second lumen. The first lumen is adapted to receive at least one of a guidewire and an implanted cardiac lead, and the second lumen is adapted to receive an inflation fluid. The device further includes an inflatable balloon carried by the catheter shaft. The inflatable balloon is adapted to receive the inflation fluid from the second lumen. The inflatable balloon includes polyurethane having a Shore A durometer of about 85 A.

A device according to paragraph [0033], wherein the first lumen and the second lumen are non-concentrically disposed within the catheter shaft.

A device according to any of paragraphs [0033]-[0034], wherein the first lumen and the second lumen are non-concentrically disposed within the catheter shaft.

A device according to any of paragraphs [0033]-[0035], further including at least one radiopaque marker carried by the catheter shaft.

A device according to any of paragraphs [0033]-[0036], wherein the at least one radiopaque marker includes a band extending around a circumference of the catheter shaft.

A device according to any of paragraphs [0033]-[0037], wherein the at least one radiopaque marker includes at least a first radiopaque marker and a second radiopaque marker.

A device according to any of paragraphs [0033]-[0038], wherein the at least one radiopaque marker further includes at least a third radiopaque marker.

A device according to any of paragraphs [0033]-[0039], wherein the inflatable balloon includes a proximal portion, a distal portion, and an intermediate portion disposed between the proximal and distal portions, wherein the first, second, and third radiopaque markers are carried within the inflatable balloon, and wherein the first radiopaque marker is axially aligned with the proximal portion, the second radiopaque marker is axially aligned with the intermediate portion, and the third radiopaque marker is axially aligned with the distal portion.

A device according to any of paragraphs [0033]-[0040], further comprising a third lumen being adapted to facilitate passage of blood from a first end to a second end of the inflatable balloon.

A device according to any of paragraphs [0033]-[0041], wherein the catheter shaft includes the third lumen.

A device according to any of paragraphs [0033]-[0042], wherein the inflatable balloon is coated with a hemostatic composition to reduce the rate of blood flow loss.

A device according to any of paragraphs [0033]-[0043], wherein the hemostatic composition comprises a fibrin-based clotting agent.

A device according to any of paragraphs [0033]-[0044], wherein the hemostatic composition comprises a coating agent.

A device according to any of paragraphs [0033]-[0045], further comprising an occlusion patch detachably carried by the inflatable balloon, the occlusion patch being deployable from the inflatable balloon to occlude the perforation.

A device according to any of paragraphs [0033]-[0046], wherein the occlusion patch includes at least one adhesive adapted to maintain a position of the occlusion patch within the blood vessel.

A device according to any of paragraphs [0033]-[0047], wherein the at least one adhesive is adapted to be activated by application of at least one of heat, pH, and light.

A device according to any of paragraphs [0033]-[0048], wherein the occlusion patch includes a scaffold structure adapted to facilitate tissue growth therein.

A device according to any of paragraphs [0033]-[0049], wherein the occlusion patch includes stem cells to facilitate bioabsorption of the occlusion patch.

A device according to any of paragraphs [0033]-[0050], wherein the occlusion patch includes at least one hormonal agent adapted to promote wound healing.

In some embodiments, a method for occluding a perforation in a blood vessel includes: (1) providing an occlusion balloon device including: a catheter shaft having a first lumen and a second lumen; an inflatable balloon carried by the catheter shaft, the inflatable balloon having a working length of about 65 mm to about 80 mm, and the inflatable balloon having an inflated diameter of about 20 mm to about 25 mm; (2) advancing the catheter shaft in the blood vessel until the inflatable balloon is positioned proximate the perforation; and (3) delivering an inflation fluid to the inflatable balloon via the second lumen to inflate the inflation balloon and thereby occlude the perforation.

A method according to paragraph [0052], wherein the inflation fluid includes saline and contrast solution.

A method according to any of paragraphs [0052]-[0053], wherein the inflation fluid includes about 80 percent saline and about 20 percent contrast solution.

A method according to any of paragraphs [0052]-[0054], wherein delivering the inflation fluid to the inflatable balloon includes delivering the inflation fluid at a pressure in the range of about 2 to about 3 atmospheres.

A method according to any of paragraphs [0052]-[0055], further comprising a third lumen being adapted to facilitate passage of blood from a first end to a second end of the inflatable balloon.

A method according to any of paragraphs [0052]-[0056], wherein the catheter shaft includes the third lumen.

A method according to any of paragraphs [0052]-[0057], wherein the inflatable balloon is coated with a hemostatic composition, and wherein delivering the inflation fluid to the inflatable balloon brings the hemostatic composition in contact with the vascular tissue at the site of the perforation.

A method according to any of paragraphs [0052]-[0058], wherein the inflatable balloon is coated with a hemostatic composition to reduce the rate of blood flow loss.

A method according to any of paragraphs [0052]-[0059], wherein the hemostatic composition comprises a fibrin-based clotting agent.

A method according to any of paragraphs [0052]-[0060], wherein the hemostatic composition comprises a coating agent.

A method according to any of paragraphs [0052]-[0061], wherein the occlusion balloon device comprises an occlusion patch detachably carried by the inflatable balloon, and delivering the inflation fluid to the inflatable balloon to inflate the inflation balloon and thereby occlude the perforation includes deploying the occlusion patch from the inflatable balloon and thereby occluding the perforation.

A method according to any of paragraphs [0052]-[0062], the occlusion patch includes at least one adhesive, and the method further comprises activating the at least one adhesive to secure the occlusion patch within the blood vessel.

A method according to any of paragraphs [0052]-[0063], activating the at least one adhesive to secure the occlusion patch within the blood vessel includes applying at least one of heat, pH, and light.

A method according to any of paragraphs [0052]-[0064], the occlusion patch includes a scaffold structure adapted to facilitate tissue growth therein.

A method according to any of paragraphs [0052]-[0065], the occlusion patch includes stem cells to facilitate bioabsorption of the occlusion patch.

A method according to any of paragraphs [0052]-[0066], the occlusion patch includes at least one hormonal agent adapted to promote wound healing.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon comprising a working portion having a length of about 115 mm to about 65 mm, and the working portion tapering inwardly from a first outer diameter to a second outer diameter.

A device according to paragraph [0068], wherein the working portion tapers inwardly from the first outer diameter to the second outer diameter at a constant slope.

A device according to any of paragraphs [0068]-[0069], wherein the working portion tapers inwardly from the first outer diameter to the second outer diameter at a constant slope.

A device according to any of paragraphs [0068]-[0070], wherein the first outer diameter is disposed at a proximal portion of the inflatable balloon and the second outer diameter is disposed at a distal portion of the inflatable balloon.

A device according to any of paragraphs [0068]-[0071], wherein the first outer diameter is in a range of about 35 mm to about 50 mm.

A device according to any of paragraphs [0068]-[0072], wherein the second outer diameter is in a range of about 16 mm to about 30 mm.

A device according to any of paragraphs [0068]-[0073], further comprising at least one radiopaque marker carried by the catheter shaft.

A device according to any of paragraphs [0068]-[0074], wherein the inflatable balloon comprises polyurethane.

A device according to any of paragraphs [0068]-[0075], wherein the inflatable balloon comprises polyurethane having a Shore A durometer of about 85 A.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon comprising polyurethane having a Shore A durometer of about 85 A, and the inflatable balloon having a working portion that tapers inwardly from a first outer diameter to a second outer diameter.

A device according to paragraph [0077], wherein the working portion tapers inwardly from the first outer diameter to the second outer diameter at a constant slope.

A device according to any of paragraphs [0077]-[0078], wherein the first outer diameter is disposed at a proximal portion of the inflatable balloon and the second outer diameter is disposed at a distal portion of the inflatable balloon.

A device according to any of paragraphs [0077]-[0079], wherein the first outer diameter is in a range of about 35 mm to about 50 mm.

A device according to any of paragraphs [0077]-[0080], wherein the second outer diameter is in a range of about 16 mm to about 30 mm.

A device according to any of paragraphs [0077]-[0081], further comprising at least one radiopaque marker carried by the catheter shaft.

A device according to any of paragraphs [0077]-[0082], wherein the inflatable balloon comprises polyurethane.

A device according to any of paragraphs [0077]-[0083], wherein the inflatable balloon comprises polyurethane having a Shore A durometer of about 85 A.

In some embodiments, a method for occluding a perforation in a blood vessel, the method comprises: providing an occlusion balloon device that comprises a catheter shaft having a first lumen and a second lumen; an inflatable balloon carried by the catheter shaft, the inflatable balloon comprising a working portion having a length of about 115 mm to about 65 mm, and the working portion tapering inwardly from a first outer diameter to a second outer diameter; advancing the catheter shaft in the blood vessel until the inflatable balloon is positioned proximate the perforation; and delivering an inflation fluid to the inflatable balloon via the second lumen to inflate the inflation balloon and thereby occlude the perforation.

A method according to paragraph [0085], wherein the inflation fluid comprises saline and contrast solution.

A method according to any of paragraphs [0085]-[0086], wherein the inflation fluid comprises about 80 percent saline and about 20 percent contrast solution.

A method according to any of paragraphs [0085]-[0087], wherein delivering the inflation fluid to the inflatable balloon comprises delivering the inflation fluid at a pressure in the range of about 2 to about 3 atmospheres.

In some embodiments, a device for occluding a perforation in a blood vessel, the device comprising: a catheter shaft having a first lumen and a second lumen, the first lumen being adapted to receive at least one of a guidewire and an implanted cardiac lead, and the second lumen being adapted to receive an inflation fluid, and an inflatable balloon carried by the catheter shaft and adapted to receive the inflation fluid from the second lumen, the inflatable balloon comprising a working portion having a length of about 115 mm to about 65 mm, wherein the working portion tapers inwardly from a first outer diameter to a second outer diameter, wherein the inflatable balloon comprises a first ratio of the length to the first outer diameter of about 1.3:1 to about 3.3:1 and a second ratio of the length to the second outer diameter of about 2.2:1 to about 7.2:1.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon comprising a working portion having a length of about 125 mm to about 85 mm, and the working portion comprising a plurality of sections each having a different outer diameter.

A device according to paragraph [0090], wherein the plurality of sections of the working portion comprises a first section having a first outer diameter; a second section having a second outer diameter; and a third section having a third outer diameter.

A device according to any of paragraphs [0090]-[0091], wherein the first outer diameter is greater than the second outer diameter and the second outer diameter is greater than the third outer diameter.

A device according to any of paragraphs [0090]-[0092], wherein the first section is proximally disposed relative to the second section and the second section is proximally disposed relative to the third section.

A device according to any of paragraphs [0090]-[0093], wherein the first outer diameter is in a range of about 60 mm to about 40 mm.

A device according to any of paragraphs [0090]-[0094], wherein the second outer diameter is in a range of about 30 mm to about 10 mm.

A device according to any of paragraphs [0090]-[0095], wherein the third outer diameter is in a range of about 26 mm to about 6 mm.

A device according to any of paragraphs [0090]-[0096], wherein the first section has a length in a range of about 18 mm to about 25 mm.

A device according to any of paragraphs [0090]-[0097], wherein the second section has a length in a range of about 52 mm to about 60 mm.

A device according to any of paragraphs [0090]-[0098], wherein the third section has a length in a range of about 20 mm to about 40 mm.

A device according to any of paragraphs [0090]-[0099], further comprising at least one radiopaque marker carried by the catheter shaft.

A device according to any of paragraphs [0090]-[0100], wherein the inflatable balloon comprises polyurethane.

A device according to any of paragraphs [0090]-[0101], wherein the inflatable balloon comprises polyurethane having a Shore A durometer of about 85 A.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon comprising polyurethane having a Shore A durometer of about 85 A, and the inflatable balloon having a working portion comprising a plurality of sections each having a different outer diameter.

A device according to paragraph [0103], wherein the plurality of sections of the working portion comprises a first section having a first outer diameter; a second section having a second outer diameter; and a third section having a third outer diameter.

A device according to any of paragraphs [0103]-[0104], wherein the first outer diameter is greater than the second outer diameter and the second outer diameter is greater than the third outer diameter.

A device according to any of paragraphs [0103]-[0105], wherein the first section is proximally disposed relative to the second section and the second section is proximally disposed relative to the third section.

A device according to any of paragraphs [0103]-[0106], wherein the first outer diameter is in a range of about 60 mm to about 40 mm.

A device according to any of paragraphs [0103]-[0107], wherein the second outer diameter is in a range of about 30 mm to about 10 mm.

A device according to any of paragraphs [0103]-[0108], wherein the third outer diameter is in a range of about 26 mm to about 6 mm.

A device according to any of paragraphs [0103]-[0109], wherein the first section has a length in a range of about 18 mm to about 25 mm.

A device according to any of paragraphs [0103]-[0110], wherein the second section has a length in a range of about 52 mm to about 60 mm.

A device according to any of paragraphs [0103]-[0111], wherein the third section has a length in a range of about 20 mm to about 40 mm.

A device according to any of paragraphs [0103]-[0112], further comprising at least one radiopaque marker carried by the catheter shaft.

A device according to any of paragraphs [0103]-[0113], wherein the inflatable balloon comprises polyurethane.

A device according to any of paragraphs [0103]-[0114], wherein the inflatable balloon comprises polyurethane.

A device according to any of paragraphs [0103]-[0115], wherein the inflatable balloon comprises polyurethane having a Shore A durometer of about 85 A.

In some embodiments, a method for occluding a perforation in a blood vessel comprises: providing an occlusion balloon device comprising: a catheter shaft having a first lumen and a second lumen; an inflatable balloon carried by the catheter shaft, the inflatable balloon comprising a working portion having a length of about 125 mm to about 85 mm, and the working portion comprising a plurality of sections each having a different outer diameter; advancing the catheter shaft in the blood vessel until the inflatable balloon is positioned proximate the perforation; and delivering an inflation fluid to the inflatable balloon via the second lumen to inflate the inflation balloon and thereby occlude the perforation.

A device according to paragraph [0117], wherein the inflation fluid comprises saline and contrast solution.

A device according to any of paragraphs [0117]-[0118], wherein the inflation fluid comprises about 80 percent saline and about 20 percent contrast solution.

A device according to any of paragraphs [0117]-[0119], wherein delivering the inflation fluid to the inflatable balloon comprises delivering the inflation fluid at a pressure in the range of about 2 to about 3 atmospheres.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon comprising a working portion having a length of about 125 mm to about 85 mm, wherein the working portion comprises: a first section having a first outer diameter, a first ratio of the length to the first outer diameter being about 1.4:1 to about 3.1:1; a second section having a second outer diameter, a second ratio of the length to the second outer diameter being about 2.8:1 to about 12.5:1; and a third section having a third outer diameter, a third ratio of the length to the third outer diameter being about 3.3:1 to about 20.8:1.

A device according to paragraph [0121], wherein the first section is proximally disposed relative to the second section and the second section is proximally disposed relative to the third section.

In some embodiments, a device for occluding a perforation in a blood vessel comprises a catheter shaft having a first lumen and a second lumen, the first lumen being adapted to receive at least one of a guidewire and an implanted cardiac lead, and the second lumen being adapted to receive an inflation fluid; and an inflatable balloon carried by the catheter shaft and adapted to receive the inflation fluid from the second lumen, the inflatable balloon having a working length of about 80 mm, and the inflatable balloon having an inflated diameter of about 20 mm.

A device according to paragraph [0123], wherein the inflatable balloon comprises polyurethane.

A device according to any of paragraphs [0123]-[0124], wherein the inflatable balloon comprises a proximal tapered portion, a distal tapered portion, and a working portion disposed between the proximal tapered portion and the distal tapered portion, the working portion having the inflated diameter of about 20 mm.

A device according to any of paragraphs [0123]-[0125], wherein the first lumen and the second lumen are non-concentrically disposed within the catheter shaft.

A device according to any of paragraphs [0123]-[0126], further comprising at least one radiopaque marker carried by the catheter shaft.

A device according to any of paragraphs [0123]-[0127], wherein the at least one radiopaque marker comprises a band extending around a circumference of the catheter shaft.

A device according to any of paragraphs [0123]-[0128], wherein the at least one radiopaque marker comprises at least a first radiopaque marker and a second radiopaque marker.

A device according to any of paragraphs [0123]-[0129], wherein the at least one radiopaque marker further comprises at least a third radiopaque marker.

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible-but possibly still flexible-catheter ("hard" catheter).

A "lead" is a conductive structure, typically an electrically insulated coiled wire. The electrically conductive material can be any conductive material, with metals and intermetallic alloys common. The outer sheath of insulative material is biocompatible and biostable (for example, non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

The term "occlude" and variations thereof as used herein refer to inhibiting flow through a structure, such as a vascular perforation.

The term "proximate" as used herein shall mean very near and/or adjacent. For example, the occlusion balloon may be very near or adjacent the perforation such that upon inflation, the occlusion balloon occludes blood flowing through the perforation.

It should be understood that every maximum numerical limitation given throughout the present disclosure is deemed to include each and every lower numerical limitation as an alternative, as if such lower numerical limitations were expressly written herein. Every minimum numerical limitation given throughout the present disclosure is deemed to include each and every higher numerical limitation as an alternative, as if such higher numerical limitations were expressly written herein. Every numerical range given throughout the present disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 11A is a partial longitudinal section view of a balloon of the occlusion balloon device of FIG. 10.

FIG. 11B is a front view of the balloon of FIG. 11A.

FIG. 17A is a side view of an occlusion balloon device according to embodiments of the present disclosure.

FIG. 17B is a front view of the occlusion balloon device of FIG. 17A.

FIG. 21 is a side view of a connection hub of the of the occlusion balloon device of FIG. 18.

FIG. 22 is a side view of the occlusion balloon device of FIG. 18 in which a balloon of the occlusion balloon device is in a deflated state and obscured by a protective cover.

DETAILED DESCRIPTION

Figure 1:
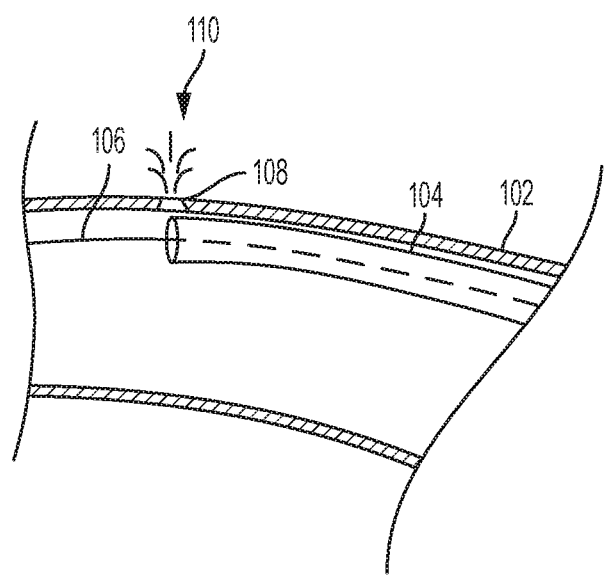
FIG. 1 is a partial cross sectional view of a vein perforated by a lead removal device during a lead removal procedure.

FIG. 1 generally shows a partial cross-sectional view of a blood vessel 102 (such as the superior vena cava, an innominate vein, a jugular vein, or the like) with an advancing lead removal catheter 104, which may include a mechanical device, a laser device or some other device, that accidentally perforates the wall of the blood vessel 102. More specifically, a cardiac lead 106 lies within the blood vessel 102. A distal end of the cardiac lead 106 (not shown) is coupled to a surgically implanted device, such as a pacemaker or defibrillator proximal to the patient's heart. The lead removal catheter 104 travels along the lead 106 from a proximal end (not shown) toward the distal end. The lead 106 may be disposed very close to a wall of the blood vessel 102 at one or more positions, such as in or near the superior vena cava or right atrium. In such a situation, as lead removal catheter 104 is advanced along the lead 106, a tip or cutting instrument of the lead removal catheter 104 (not shown) may accidentally create a perforation 108 in the wall of the blood vessel 102, thereby causing bleeding 110.

Factors contributing to the occurrence of the perforation 108 may include the following: the sharpness of the bend in the lead 106; the structural integrity of the wall of the blood vessel 102 at positions in which the lead 106 is very close to the wall of the blood vessel 102; sharp bends in the blood vessel 102; the speed and/or force applied to the lead removal catheter 104 to advance the catheter 104; and/or various combinations of these and other factors known to those skilled in the art. In any case, upon detection of the perforation 108 (for example, via fluoroscopy, blood pressure monitoring, or the like), the lead removal catheter 104 may be immediately removed from the vasculature, and the one or more of the occlusion balloon devices according to embodiments of the present disclosure may be inserted into the vasculature and located adjacent the perforation 108 and employed to occlude the perforation 108. That is, an occlusion balloon device may be inserted into the blood vessel and occlude the perforation 108 while the lead removal catheter 104 remains in the blood vessel 102 or the lead removal catheter 104 may be removed from the blood vessel 102 prior to insertion and deployment of the occlusion balloon device in the blood vessel 102.

Figure 2:
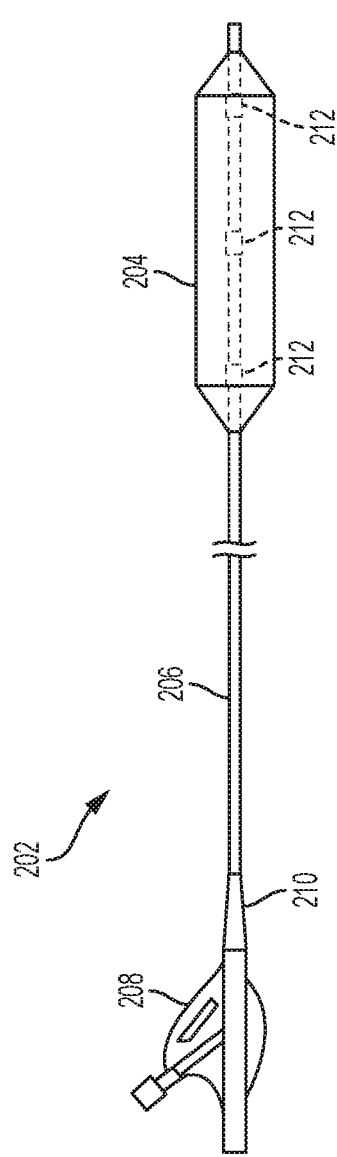
FIG. 2 is a side view of an occlusion balloon device according to embodiments of the present disclosure.

FIG. 2 is a side view of an exemplary occlusion balloon device 202 device according to embodiments of the present disclosure. The occlusion balloon device 202 generally includes an inflatable balloon 204 that is carried at a distal portion of a catheter shaft 206. The occlusion balloon device 202 also includes a connection hub 208 that is carried at a proximal portion of the catheter shaft 206. The connection hub 208 and the catheter shaft 206 may carry a distally-tapering strain relief 210 at an interface therebetween. The catheter shaft 206 may also carry one or more radiopaque markers 212 such that the position of the occlusion balloon device 202 may be determined via medical imaging (for example, via fluoroscopy). The catheter shaft 206 may carry, for example, three radiopaque markers 212 as shown in FIG. 2. A first radiopaque marker 212 may be axially aligned with a proximal portion of the inflatable balloon 204, a second radiopaque marker 212 may be axially aligned with an intermediate portion of the inflatable balloon 204, and a third radiopaque marker 212 may be axially aligned with a distal portion of the inflatable balloon 204.

Figure 3:
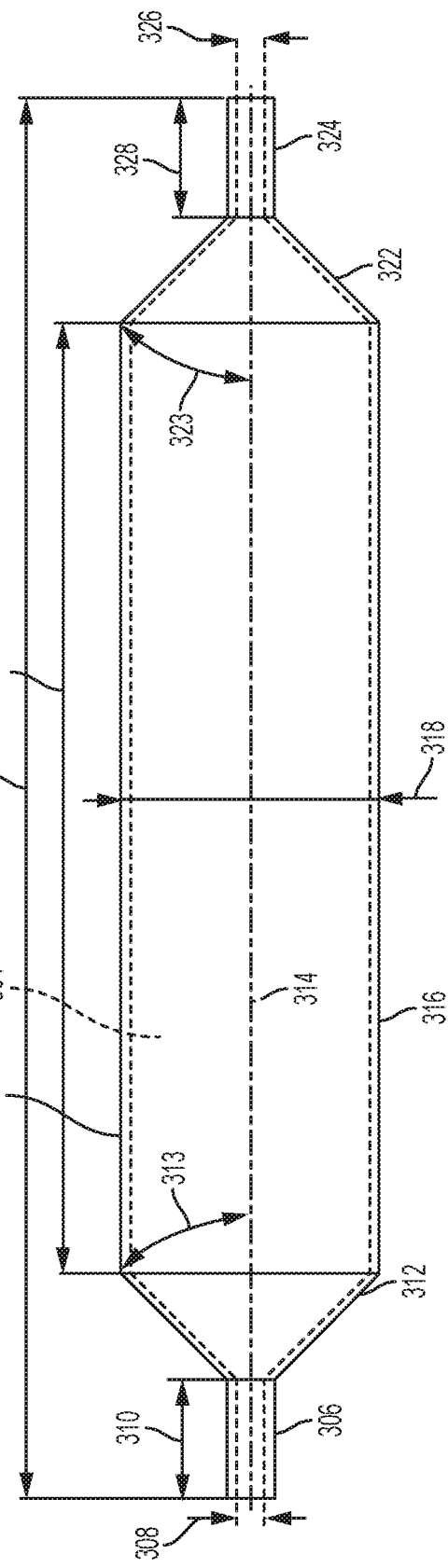
FIG. 3 is a side view of a balloon of the occlusion balloon device of FIG. 2.

FIG. 3 is a side view of the inflatable balloon 204 of the occlusion balloon device 202 of FIG. 2, wherein the inflatable balloon 204 is depicted in an inflated state. The inflatable balloon 204 may include a wall 302, an inflation chamber 304, an overall length 305, a proximal neck 306 having a length 310, a distal neck 324 having a length 328, a working portion 316 having a length 320, a proximal tapered portion 312 disposed between the proximal neck 306 and the working portion 316, and a distal tapered portion 322 disposed between the distal neck 324 and the working portion 316.

The wall 302 of the inflatable balloon 204 defines an inflation chamber 304. The inflation chamber 304 is adapted to receive an inflation fluid (for example, about 80 percent saline (that is, 80 percent±5 percent) and about 20 percent contrast solution (that is, 20 percent±5 percent)) that inflates the balloon. Upon a clinician introducing the lead removal catheter 104 into the vasculature, positioning the inflatable balloon 204 adjacent the perforation 108 and inflating the inflatable balloon, the inflatable balloon 204 facilitates occlusion of the perforation 108.

In some embodiments, the inflatable balloon 204 is formed of one or more relatively compliant materials. Such materials facilitate filling vessels of different diameters, vessels having irregularities, and/or vessels carrying implanted objects (such as cardiac leads) without imparting relatively high dilation forces on a vessel. The inflatable balloon 204 may be formed of one or more elastomeric materials, such as polyurethane. For example, the inflatable balloon 204 may be formed of Pellethane®, specifically 80AE Pellethane®, which is available from The Lubrizol Corporation of Wickliffe, Ohio. The inflatable balloon 204 may have a Shore A durometer of about 85 A (that is, 85 A±4 A).

The inflatable balloon 204 may have an overall length 305 of about 98 mm (that is, 98 mm±3 mm) to about 82 mm (that is, 82 mm±3 mm).

The inflatable balloon 204 includes a proximal neck 306 that engages the catheter shaft 206 (via one or more adhesives, a compression fit, or the like). The proximal neck 306 may have an inner diameter 308 of about 2.5 mm (that is, 2.5 mm±0.07 mm). The proximal neck 306 may have a length 310 of about 10 mm (that is, 10 mm±1 mm). The proximal neck 306 may have a wall thickness of about 0.24 mm (that is, 0.24 mm±0.01 mm).

Distal to the proximal neck 306, the proximal neck 306 couples to a proximal tapered portion 312. The proximal tapered portion 312 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 204 is inflated, the proximal tapered portion 312 may be disposed at an angle 313 of about 45 degrees (that is, 45 degrees±0.5') relative to a longitudinal axis 314 of the inflatable balloon 204.

Distal to the proximal tapered portion 312, the proximal tapered portion 312 couples to a working portion 316. The working portion 316, when the inflatable balloon 204 is appropriately positioned and inflated, occludes the perforation 108. The working portion 316 may have an inflated outer diameter 318 of about greater than 20 mm (that is, 20 mm±2 mm), for example between about 20 mm (that is, 20 mm±2 mm) and 30 mm (that is, 30 mm±2 mm) and possibly further between about 20 mm (that is, 20 mm±2 mm) and about 25 mm (that is, 25 mm±2 mm). The working portion 316 may have a length 320 of about 80 mm (that is, 80 mm±3 mm) to about 65 mm (that is, 65 mm±3 mm). The working portion 316 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). The ratio of the length 320 of the working portion 302 to the outer diameter 318 of the inflatable balloon 204 in the inflated state is, therefore, about 2.6:1 to about 4:1. Having this ratio with a relatively constant inflated outer diameter 318 of about 20 mm to about 25 mm for a length 320 of about 80 mm to about 65 mm increases the likelihood that the inflatable balloon 204 will occlude the perforation 108 when placed adjacent the perforation 108 in the patient vasculature and inflated. That is, the length 320 of the working portion 302 of the inflatable balloon 204 is designed to be substantially longer than the perforation 108, thereby potentially increasing the clinician's ability to quickly locate and occlude the perforation.

As mentioned above, the working portion 316 of the inflatable balloon 204 may have an inflated outer diameter 318 of about greater than 20 mm (that is, 20 mm±2 mm), for example between about 20 mm (that is, 20 mm±2 mm) and about 30 mm (that is, 30 mm±2 mm) and possibly further between about 20 mm (that is, 20 mm±2 mm) and about 25 mm (that is, 25 mm±2 mm). Inflating the outer diameter 318 of the working portion 316 of the inflatable balloon 204 to this diameter increases the likelihood that the working portion 316 of the inflatable balloon 204 will be about the same diameter or slightly larger than the diameter of the blood vessel 102 at the perforation 108. Inflating the outer diameter 318 of the working portion 316 of the inflatable balloon 204 to be about the same diameter or slightly larger than the diameter of the blood vessel 102 at the perforation 108 increases the likelihood that the inflatable balloon 204 will block the perforation 108 without increasing its size.

Again, the inflatable balloon 204 may be formed of one or more elastomeric materials, such as polyurethane. To inflate the inflatable balloon 204 to the range of diameters referenced above, it may also be desirable to inflate the inflatable balloon 204 with an inflation fluid to a pressure within the balloon inflation chamber 304 from about 0 psi to about 3 psi. The amount of inflation fluid used to inflate the inflatable balloon 204 to such a pressure and/or at the desired diameter is about 20 ml (cc) to about 60 ml (cc).

Distal to the working portion 316, the working portion 316 couples to a distal tapered portion 322. The distal tapered portion 322 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 204 is inflated, the distal tapered portion 322 may be disposed at an angle 323 of about 45 degrees (that is, 45 degrees±0.5') relative to the longitudinal axis 314.

Distal to the distal tapered portion 322, the distal tapered portion 322 couples to a distal neck 324 that engages the catheter shaft 206 (via one or more adhesives, a compression fit, or the like). The distal neck 324 may have an inner diameter 326 of about 2.5 mm (that is, 2.5 mm±0.07 mm). The distal neck 324 may have a length 328 of about 10 mm (that is, 10 mm±1 mm). The distal neck 324 may have a wall thickness of about 0.24 mm (that is, 0.24 mm±0.01 mm).

Figure 4:
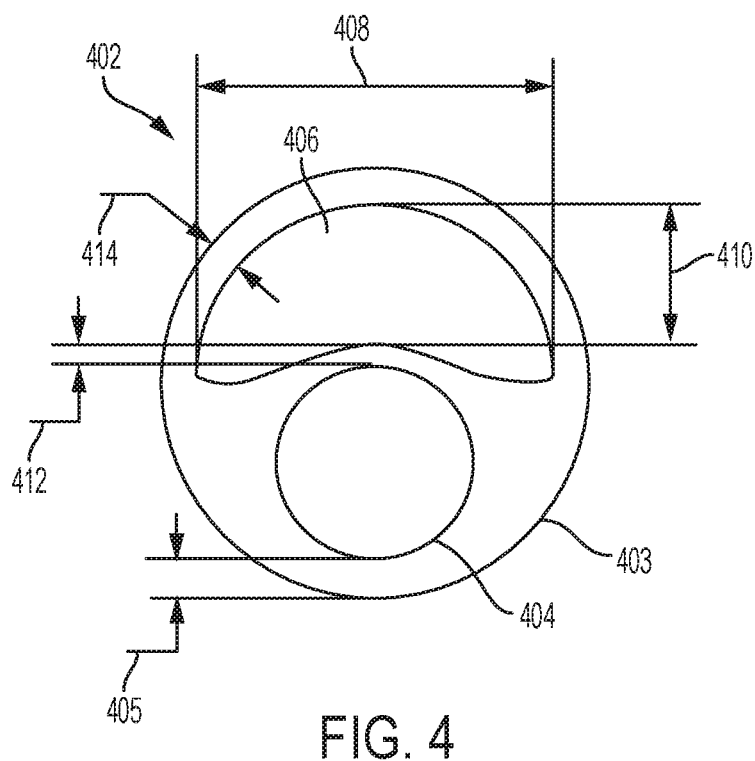
FIG. 4 is a cross-sectional view of an embodiment of a catheter shaft of the occlusion balloon device of FIG. 2.

FIG. 4 is a cross-sectional view of a first exemplary embodiment of a catheter shaft 402 that may be used as the catheter shaft 206 described above. The catheter shaft 402 may be formed of one or more elastomeric materials, such as polyurethane. For example, the catheter shaft 402 may be formed of Pellethane®, specifically 75D Pellethane®, which is available from The Lubrizol Corporation.

The catheter shaft 402 may have an outer diameter 403 of about 2.1 mm (that is, 2.1 mm±0.038 mm). The catheter shaft 402 may have a length of about 110 cm (that is, 110 cm±0.3 cm).

The catheter shaft 402 includes a first lumen 404 that is adapted to receive a guidewire or an implanted cardiac lead to guide the occlusion balloon device 202 to a position proximate the perforation 108. The first lumen 504 may, therefore, also be referred to as a guidewire lumen or an implanted lead lumen. The first lumen 404 is non-centrically disposed relative to the outer diameter 403 of the catheter shaft 402. Assuming that the first lumen 404 is adapted to receive a guidewire, the first lumen 404 may have circular cross section and have a diameter of about 0.94 mm (that is, 0.94 mm±0.025 mm). Again, assuming that the first lumen 404 is adapted to receive a guidewire, a minimum wall thickness 405 between the first lumen 404 and the outer diameter 403 may be about 0.15 mm (that is, 0.15 mm±0.025 mm). If, however, the first lumen 404 is adapted to receive an implanted cardiac lead, the first lumen 404 may have a larger circular cross section because the diameter of a cardiac lead is typically greater than 0.25 mm. Accordingly, the first lumen 404 may have a circular cross section greater than 0.25 mm. Also, although the first lumen 404 is depicted as having a circular cross section, the cross-sectional shape of the first lumen 404 may have a non-circular section, such as an oval.

The catheter shaft 402 also includes a second lumen 406 that is adapted to receive the inflation fluid from the connection hub 208 and deliver the inflation fluid to the balloon inflation chamber 304. The second lumen 506 may, therefore, also be referred to as an inflation lumen. The second lumen 406 is non-centrically disposed relative to the first lumen 404 and the outer diameter 403 of the catheter shaft 402. The second lumen 406 may have a circular cross section or a non-circular cross-sectional shape, such as a crescent-like cross-sectional shape. Assuming that the second lumen 406 has a crescent-like cross-sectional shape, the second lumen 406 may have a width 408 of about 1.8 mm (that is, 1.8 mm±0.025 mm). The second lumen 406 may have a height 410 in a plane that bisects the catheter shaft 402 of about 0.76 mm (that is, 0.76 mm±0.025 mm). It is desirable to introduce as much inflation fluid through the second lumen 406 and into the inflation chamber of the inflatable balloon as quickly as possible, in order to inflate the inflatable balloon as quickly as possible and minimize potential blood loss through the perforation. Accordingly, it is desirable to have as large as possible a cross-sectional area for the second lumen 406 for a given outer diameter 403 of the catheter shaft 402. For example, for an outer diameter 403 of 2.1 mm (that is, 2.1 mm±0.038 mm) to an outer diameter of 2.3 mm (that is, 2.3 mm±0.038 mm), the cross-sectional area for the second lumen 406 may be between 0.65 mm$^2$ and 1.90 mm$^2$ or any increment of 0.01 mm$^2$ therebetween, such as 0.66, 0.67, 0.68, 0.69, 0.70 . . . 1.0 . . . 1.5 . . . 1.9 mm$^2$.

A minimum wall thickness 412 between the second lumen 406 and the first lumen 404 may be about 0.1 mm (that is, 0.1 mm±0.025 mm). A minimum wall thickness 414 between the second lumen 406 and the outer diameter 403 may be about 0.15 mm (that is, 0.15 mm±0.025 mm). Having two or more of the following allows the clinician to quickly inflate the inflation chamber 304 of inflatable balloon 204 with the inflation fluid: a crescent-like cross-sectional shape for the second lumen 406; a wall thickness 405 between the first lumen 404 and the outer diameter 403 about 0.15 mm; a wall thickness 414 between the second lumen 406 and the outer diameter 403 about 0.15 mm; and wall thickness 412 between the second lumen 406 and the first lumen 404 about 0.1 mm.

The catheter shaft 402 also includes one or more apertures (not shown) that couple the second lumen 406 to the exterior of the catheter shaft 402 and the balloon inflation chamber 304. That is, the second lumen 406 delivers the inflation fluid to the inflatable balloon 204 via one or more apertures. The second lumen 406 may be covered at the distal end of the catheter shaft 402 (for example, by a separate cover, the wall of the catheter shaft 402, or the like).

Figure 5:
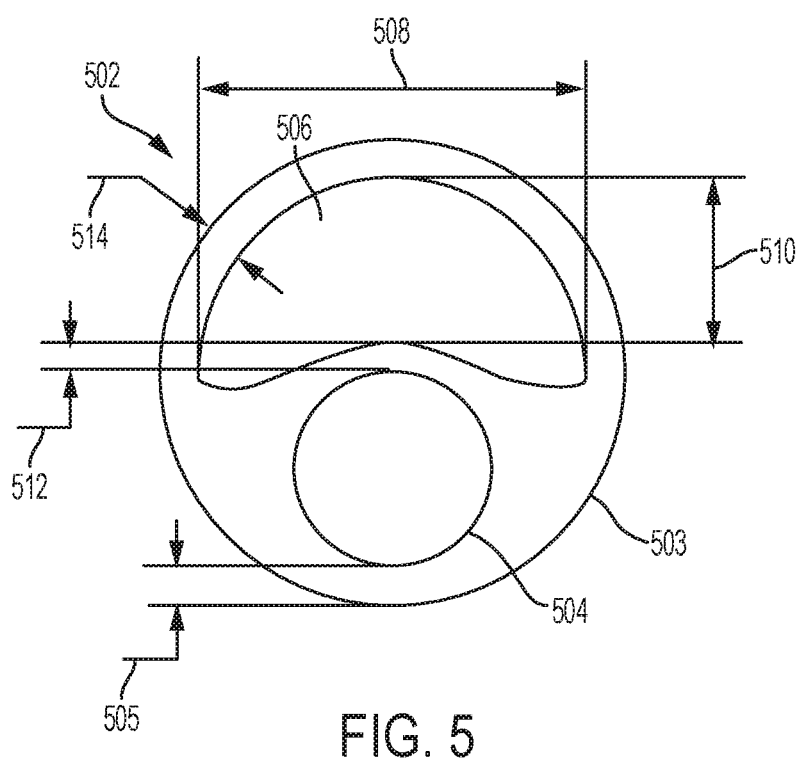
FIG. 5 is a cross-sectional view of another embodiment of a catheter shaft of the occlusion balloon device of FIG. 2.

FIG. 5 is a cross-sectional view of a second exemplary embodiment of a catheter shaft 502 that may be used as the catheter shaft 206 described above. The catheter shaft 502 may be formed of one or more elastomeric materials, such as polyurethane. For example, the catheter shaft 502 may be formed of Pellethane®, specifically 75D Pellethane®, which is available from The Lubrizol Corporation.

The catheter shaft 502 may have an outer diameter 503 of about 2.3 mm (that is, 2.3 mm±0.038 mm). The catheter shaft 502 may have a length of about 110 cm (that is, 110 cm±0.3 cm).

The catheter shaft 502 includes a first lumen 504 that is adapted to receive a guidewire or an implanted cardiac lead to guide the occlusion balloon device 202 to a position proximate the perforation 108. The first lumen 504 is non-centrically disposed relative to the outer diameter 503 of the catheter shaft 502. The first lumen 504 may have circular cross section and have a diameter of about 0.94 mm (that is, 0.94 mm±0.025 mm). A minimum wall thickness 505 between the first lumen 504 and the outer diameter 503 may be about 0.1 mm (that is, 0.1 mm±0.025 mm).

The catheter shaft 502 also includes a second lumen 506 that is adapted to receive the inflation fluid from the connection hub 208 and deliver the inflation fluid to the balloon inflation chamber 304. The second lumen 506 is non-centrically disposed relative to the first lumen 504 and the outer diameter 503 of the catheter shaft 502. The second lumen 506 may have a non-circular cross-sectional shape, such as a crescent-like cross-sectional shape. The second lumen 506 may have a width 508 of about 2.0 mm (that is, 2.0 mm±0.025 mm). The second lumen 506 may have a height 510 in a plane that bisects the catheter shaft 502 of about 0.94 mm (that is, 0.94 mm±0.025 mm). A minimum wall thickness 512 between the second lumen 506 and the first lumen 504 may be about 0.1 mm (that is, 0.1 mm±0.025 mm). A minimum wall thickness 514 between the second lumen 506 and the outer diameter 503 may be about 0.15 mm (that is, 0.15 mm±0.025 mm). Having a two or more of the following allows the clinician to quickly inflate the inflation chamber 304 of inflatable balloon 204 with the inflation fluid: a crescent-like cross-sectional shape for the second lumen 506; a wall thickness 505 between the first lumen 504 and the outer diameter 503 about 0.15 mm; a wall thickness 514 between the second lumen 506 and the outer diameter 503 about 0.1 mm; and wall thickness 512 between the second lumen 506 and the first lumen 504 about 0.1 mm.

The catheter shaft 502 also includes one or more apertures (not shown) that couple the second lumen 506 to the exterior of the catheter shaft 502 and the balloon inflation chamber 304. That is, the second lumen 506 delivers the inflation fluid to the inflatable balloon 204 via one or more apertures. The second lumen 506 may be covered at the distal end of the catheter shaft 502 (for example, by a separate cover, the wall of the catheter shaft 502, or the like).

In some embodiments, the dimensions and material properties of the inflatable balloon 204, the catheter shaft 402, and the catheter shaft 502 facilitate using the occlusion balloon device 202 with relatively small guidewires and introducer sheaths and relatively quickly delivering the inflation fluid to the inflatable balloon 204 (for example, in 15 seconds or less). Furthermore, the occlusion balloon device 202 has sufficient strength for entering a subject's vasculature and occluding a vascular perforation.

Figure 6B:
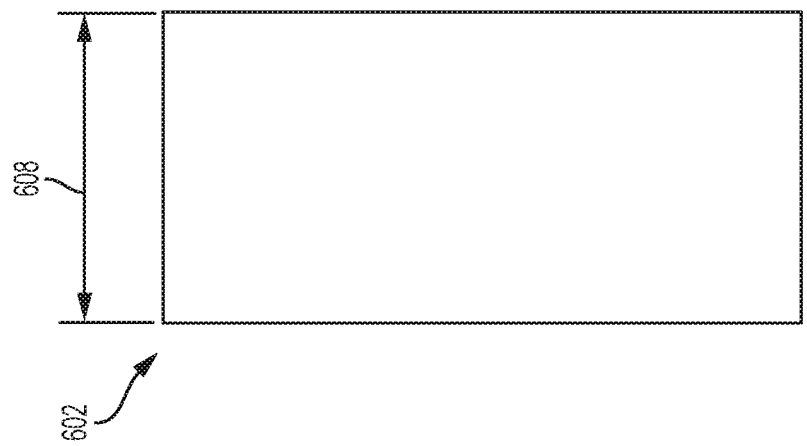
FIG. 6B is a side view of the radiopaque marker band of FIG. 6A.
Figure 6A:
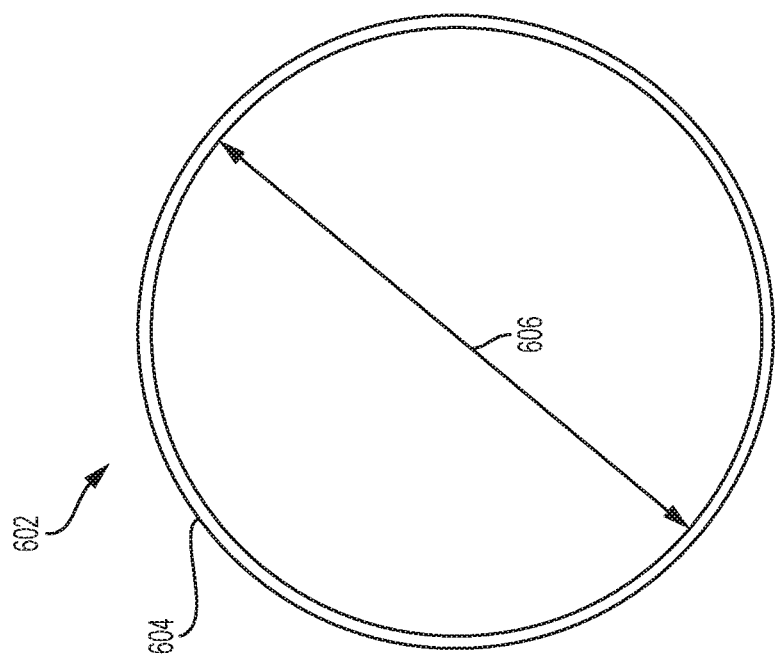
FIG. 6A is a front view of a radiopaque marker band of the occlusion balloon device of FIG. 2.
Figure 7A:
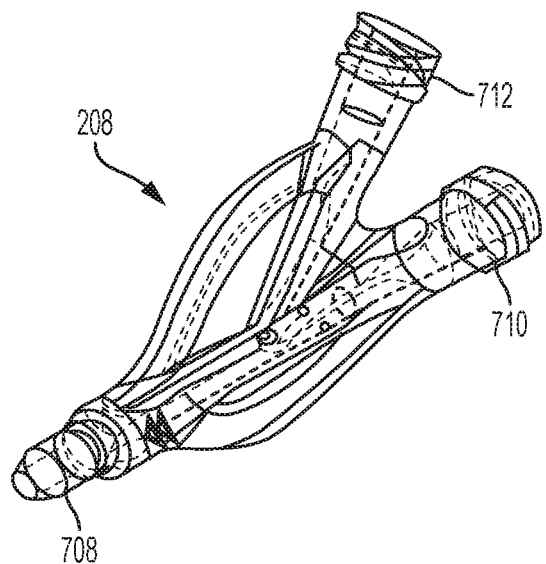
FIG. 7A is a perspective view of a connection hub of the of the occlusion balloon device of FIG. 2.
Figure 7B:
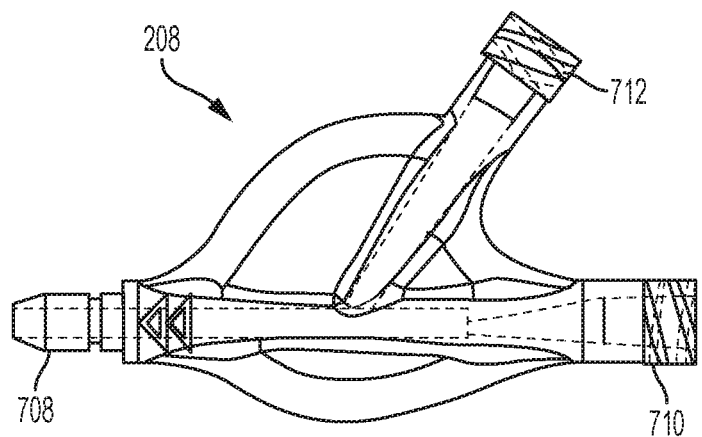
FIG. 7B is a side view of the connection hub of FIG. 7A.
Figure 7C:
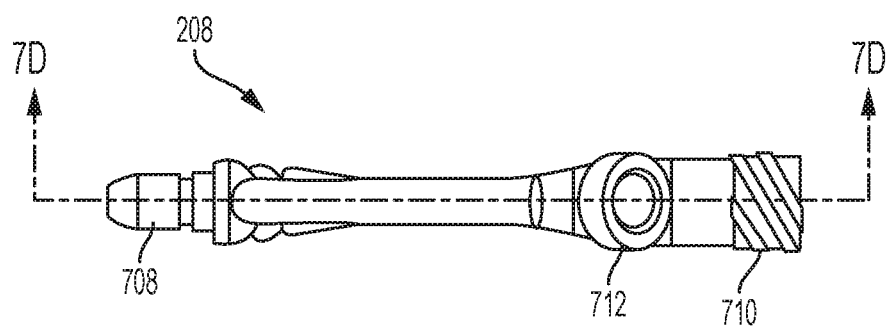
FIG. 7C is a top view of the connection hub of FIG. 7A.
Figure 7D:
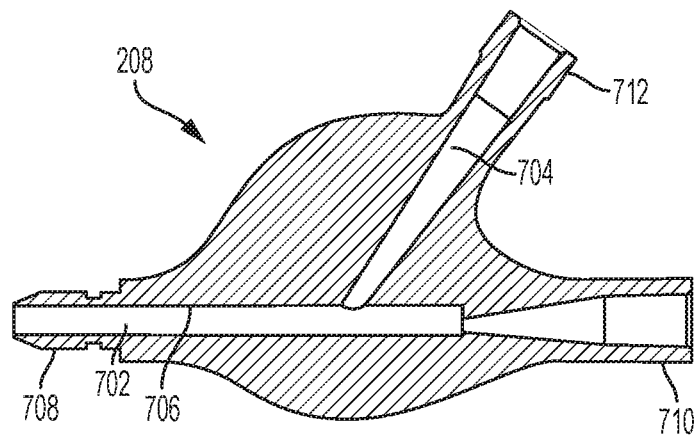
FIG. 7D is a side sectional view of the connection hub along line 7D-7D of FIG. 7C.

FIGS. 6A and 6B are views of a radiopaque marker band 602 that may be used as the radiopaque markers 212 described above. The radiopaque marker band 602 may be formed of one or more radiopaque materials, such a mixture of about 90 percent platinum (that is, 90 percent±1 percent) and 10 percent iridium (that is, 10 percent±1 percent). The radiopaque marker band 602 may have an open-ended cylindrical shape that is adapted to extend around the circumference of the catheter shaft 206. The radiopaque marker band 602 may have an outer diameter 604 in a range of about 2.3 mm (that is, 2.3 mm±0.01 mm) to about 2.5 mm (that is, 2.5 mm±0.01 mm). The radiopaque marker band 602 may have an inner diameter 606 of about 2.2 mm (that is, 2.2 mm±0.01 mm) to about 2.4 mm (that is, 2.4 mm±0.01 mm). The radiopaque marker band 602 may have a length 608 of about 1.2 mm (that is, 1.2 mm±0.05 mm).

FIGS. 7A-7D are views of the connection hub 208. The connection hub 208 may be formed of one or more polymers, such as Polycarbonate, specifically Makrolon®, which is available from Bayer MaterialScience of Darmstadt, Germany. The connection hub 208 includes a bifurcate lumen, which in turn includes a main lumen 702 and a branch lumen 704 (see FIG. 7D). The branch lumen 704 extends from the main lumen 702 at an acute angle. The main lumen 702 may have an inner diameter 706 in a range of about 2.2 mm (that is, 2.2 mm±0.025 mm) to about 2.4 mm (that is, 2.4 mm±0.025 mm). The main lumen 704 couples to a first port 708 on a distal side of the connection hub 208. The first port 708 couples to the catheter shaft 206 and the strain relief 210. The main lumen 704 couples to a second port 710 on a proximal side of the connection hub 208. The second port 710, which may be, for example, ISO 594-complaint Luer connector, is adapted to receive a guidewire and/or couple to an inflation fluid source, such as a syringe. The branch lumen 706 couples to a third port 712 on the proximal side of the connection hub 208. The third port 712, which may be, for example, ISO 594-complaint Luer connector, is adapted to receive a guidewire and/or couple to an inflation fluid source, such as a syringe.

Figure 8A:
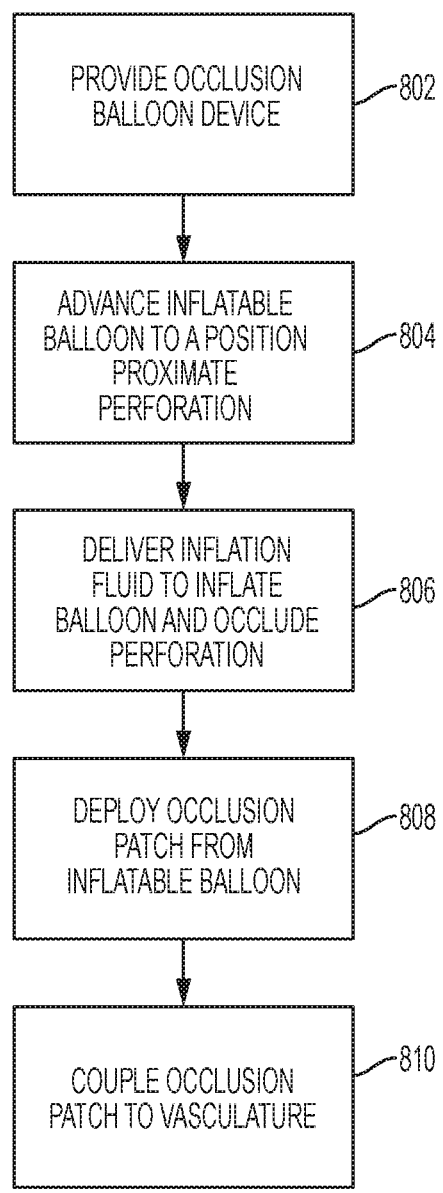
FIG. 8A illustrates an exemplary method for occluding a perforation in a blood vessel according to embodiments of the present disclosure.
Figure 8B:
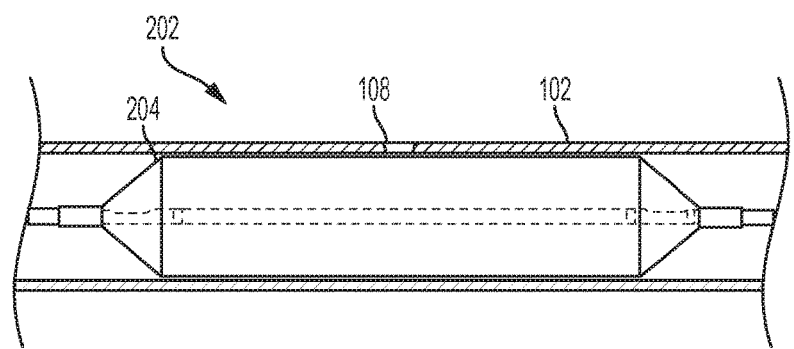
FIG. 8B illustrates an exemplary occlusion balloon occluding a perforation in a blood vessel according to embodiments of the present disclosure.

FIG. 8A illustrates an exemplary method for occluding a perforation in a blood vessel according to embodiments of the present disclosure. The method begins at block 802 by providing an occlusion balloon device, such as the occlusion balloon device 202 of depicted in FIGS. 2-7 described above or any of the occlusion balloon devices, such as the occlusion balloon devices depicted in FIGS. 9-22, described below. For simplicity, this paragraph only refers to the features of the occlusion balloon device 202. At block 804, the catheter shaft 206 and the inflatable balloon 204 are advanced in the blood vessel until the inflatable balloon 204 is positioned proximate a perforation, as depicted in FIG. 8B. Continuing to refer to FIG. 8B, the inflatable balloon 204 is in an inflated state adjacent and, therefore, proximate the perforation 108. Although the inflatable balloon 204 in depicted in FIG. 8B as adjacent and covering the entire perforation 108, the occlusion balloon device 202 could be placed in a position within the blood vessel 102 such that the inflatable balloon 204 covers only a portion of the perforation 108 or the inflatable balloon 204 does not cover any portion of the perforation 108 but is disposed very near the perforation 108 in a location that is upstream of the blood flow within the blood vessel, thereby allowing the inflatable balloon 204 to occlude the blood flow from flowing through the perforation 108.

Referring again to FIG. 8A, in some embodiments, the first lumen 404 of the catheter shaft 206 receives a guidewire or an implanted cardiac lead, and the catheter shaft 206 and the inflatable balloon 204 are advanced along the guidewire or the implanted cardiac lead. In some embodiments, the catheter shaft 206 may be advanced to the perforation via a femoral vein (for example, the right femoral vein) by using a femoral introducer sheath (for example, a 12F femoral introducer sheath). In some embodiments, the catheter shaft 206 may be advanced until the proximal radiopaque marker 212 is located at the junction of the superior vena cava and right atrium. At block 806, an inflation fluid (for example, saline and contrast solution as described above) is delivered to the inflatable balloon 204 via the second lumen 406 of the catheter shaft 206 to inflate the inflation balloon 204 and thereby occlude the perforation. In some embodiments, a 60 ml (cc) syringe delivers the inflation fluid to the inflation balloon 204 until the balloon 204 conforms to the vasculature. In some embodiments, the inflation fluid is delivered to the inflatable balloon 204 at a pressure in the range of about 2 atmospheres (that is, 2 atmospheres±10 percent) to about 3 atmospheres (that is, 3 atmospheres±10 percent). In some embodiments, contrast is injected via a superior venous access site to confirm proper inflation of the balloon 204 and occlusion of the perforation. In some embodiments, stabilization of the patient's hemodynamic and/or vital signs may be used to confirm occlusion of the perforation. In some embodiments and at block 808, the method may optionally include deploying an occlusion patch (for example, the occlusion patch 1708 described below) from the inflatable balloon 204 over the vascular perforation to thereby occlude the perforation. And if the inflatable balloon 204 includes an occlusion patch, inflation of the balloon 204 causes deployment of the occlusion patch. Additionally, in some embodiments and at block 810, the method optionally includes coupling the occlusion patch to the vasculature to maintain the position of the patch within the vasculature. In some embodiments, coupling the occlusion patch to the vasculature includes activating one or more adhesives carried by the patch in any of the manners described below. In some embodiments, when occlusion is no longer needed, the balloon 204 may be deflated by applying suction to the second lumen 406 by using a 60 ml (cc) syringe. In some embodiments, deflation of the balloon 204 may be confirmed by using fluoroscopy.

Figure 9A:
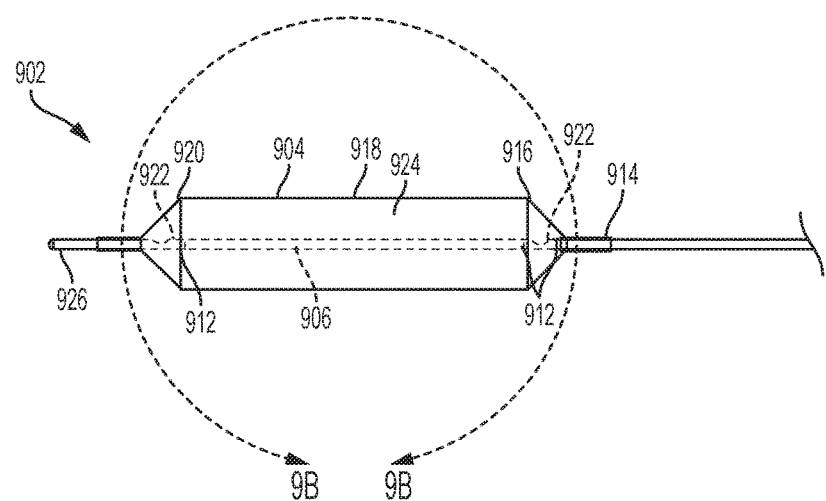
FIG. 9A is a partial side view of an occlusion balloon device according to embodiments of the present disclosure.
Figure 9B:
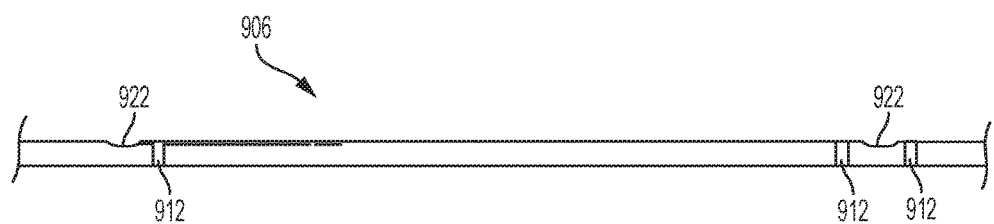
FIG. 9B is a detail view of a catheter shaft of the occlusion balloon device within line 9B-9B of FIG. 9A.

FIGS. 9A and 9B are side views of a distal portion of another exemplary occlusion balloon device 902 device according to embodiments of the present disclosure. The occlusion balloon device 902 generally includes an inflatable balloon 904, which may be similar to the balloons described above. The inflatable balloon 904 is carried at a distal portion of a catheter shaft 906. The occlusion balloon device 902 also includes a connection hub (not shown), which may be similar to the connection hubs described above. The connection hub is carried at a proximal portion of the catheter shaft 906. The connection hub and the catheter shaft 906 may carry a distally-tapering strain relief (not shown), which may be similar to the strain reliefs described above, at an interface therebetween. The catheter shaft 906 may also carry one or more radiopaque markers 912 such that the position of the occlusion balloon device 902 may be determined via medical imaging (for example, via fluoroscopy). The catheter shaft 906 may carry, for example, three radiopaque markers 912 as shown in FIGS. 9A and 9B. A first radiopaque marker 912 may be axially aligned with an intersection of a proximal neck 914 of the balloon 904 and a proximal tapered portion 916 of the balloon 904. A second radiopaque marker 912 may be axially aligned with the intersection of the proximal tapered portion 916 and a working portion 918 of the balloon 904. A third radiopaque marker 912 may be axially aligned with the intersection of the working portion 918 and a distal tapered portion 920 of the balloon 904.

The inflatable balloons of the present disclosure can be treated or coated with a variety of pharmaceutical and biological agents to assist in the treatment of the perforation site. In some embodiments, the inflatable balloons of the present disclosure can be coated with a hemostatic composition to reduce the rate of blood flow loss and allow more time for planning and initiating surgical repair of the perforation site. Generally, the hemostatic composition includes one or more hemostatic blood clotting agents (also referred to as hemostatic agents or clotting agents). Suitable clotting agents are present in effective amounts in the hemostatic composition such that they can stimulate or facilitate hemostasis. Suitable clotting agents include, but are not limited to: thrombin, or any naturally-occurring or synthetic agent that converts fibrinogen to fibrin; calcium, sodium, magnesium or other chemical ions that stimulate hemostasis; protamine sulfate; an epsilon amino caproic acid, fibrinogen, chitin, and the like. Hemostatic agents that can be used as part of the hemostatic compositions of the present disclosure also include, but are not limited to, fibrin-based agents such as fibrin sealant (also referred to as fibrin glue), gelatin matrix thrombin, gelatin sponge, oxidized cellulose, collagen sponge, collagen fleece, recombinant factor VIIa, and the like.

In some embodiments, it is also advantageous to include in the hemostatic compositions one or more agents having cell or tissue adhesion properties, including but not limited to, polyethylene glycol, cyanoacrylate, fibronectin, von Willebrand factor, protein Z and the like. Agents having cell or tissue adhesion properties can further reduce the rate of blood flow loss from a vascular perforation as well as promote healing of the perforation wound site. It may also be advantageous to include in the hemostatic compositions one or more coating agents, including but not limited to, a lipophilic antioxidant, such as nordihydroguaiaretic acid, resveratrol, propyl gallate and the like, with or without the addition of a biocompatible polymer, to stabilize the composition and/or prevent premature loss of the composition as the balloon travels through the vasculature to the perforation site.

Other components of the hemostatic composition can include hormonal agents, such as growth factors to promote wound healing and other therapeutic agents. In some embodiments, the hemostatic composition includes a wound-sealant composition and/or a cross-bridging binding agent of silica nanoparticles having potential reactive surface hydroxyl groups and possibly additional components including, for example, a fluid removal agent, a dehydration agent, an adhesive clumping agent, a swelling agent, a drug delivery vehicle such as a nanoparticle or microparticle, a clot enhancing composition, an activator or accelerator and the like. In other embodiments, the hemostatic composition can include prophylactic antibiotics and bactericidal agents such as penicillins, penicillin combinations, sulfonamides, lincosamides, carbapenems, tetracyclines, aminoglycosides, as well as other suitable antibiotic compositions and combinations thereof. The hemostatic composition of the present disclosure can also contain suitable adjuvants and excipients including preservative agents, wetting agents, emulsifying agents and dispersing agents, additional antibiotics alone or in combination with antifungal agents, for example, parabens, chlorobutanol, phenol, sorbic acid, and the like. It is also possible to include osmoregulation agents such as sugars, sodium chloride and the like. Additionally, agents for delaying absorption, such as aluminum monostearate and gelatin, can also be included in the hemostatic composition. As one of ordinary skill in the art would readily recognize based on the present disclosure, the hemostatic compositions can be formulated to be a powder, spray, aerosol, foam or gel that can be directly applied to the perforation site.

The hemostatic compositions of the present disclosure can be delivered to the tissues of the perforation site in various manners. For example, the hemostatic compositions can be applied to the outside periphery of an inflatable balloon positioned at the distal end of a catheter, such that when the balloon is inflated to occlude the perforation, the hemostatic composition is brought into contact with the tissue of the perforation site. Once delivered to the tissue of the perforation site, the different components of the hemostatic composition can exert their biological effects, such as promoting blood clotting and/or cell and tissue adhesion, in order to reduce the rate of blood flow loss and to promote healing of the perforation site. In some embodiments, the composition can be applied to the folds of inflatable balloon (in its uninflated state) such that the composition is protected from premature loss as the distal end of the catheter is being positioned in the vasculature. Upon deployment of the balloon, the composition is exposed and can be delivered to the tissue of the perforation site.

In other embodiments, devices and mechanisms can be included in the distal end of the catheter, adjacent to the balloon, to facilitate the expulsion of the composition to the tissue of the perforation site. For example, one or more optical fibers can be used to deliver a pulse of light energy to liquid media (e.g., contrast media) contained within an inflatable balloon in order to create a shock wave (e.g., cavitation of the liquid media) that propagates radially and delivers the composition to the tissue of the perforation site. Other means for delivering the hemostatic composition to the tissue of the perforation site can also be used, as would be recognized by one of ordinary skill in the art based on the present disclosure.

The catheter shaft 906 may include first and second lumens (not shown) that are similar to the first and second lumens, respectively, described above. The catheter shaft 906 also includes one or more apertures 922 that couple the second lumen to the exterior of the catheter shaft 906 and the balloon inflation chamber 924. That is, the second lumen delivers the inflation fluid to the inflatable balloon 904 via one or more apertures 922. The catheter shaft 906 may include, for example, two apertures 922 as shown in FIGS. 9A and 9B. A first aperture 922 may be axially aligned with the proximal tapered portion 916 of the balloon 904. A second aperture 922 may be axially aligned with the distal tapered portion 920 of the balloon 904.

A distal end of the catheter shaft 906 carries a distal tip 926 that covers the second lumen of the catheter shaft 906. The distal tip 926 includes an opening (not shown) that is aligned with the first lumen of the catheter shaft 906. Together with the first lumen, the opening is adapted to receive a guidewire or an implanted cardiac lead. The distal tip 926 may be formed of one or more elastomeric materials, such as polyurethane. For example, the distal tip 926 may be formed of Pellethane®, specifically 65D Pellethane®, which is available from The Lubrizol Corporation.

Figure 10:
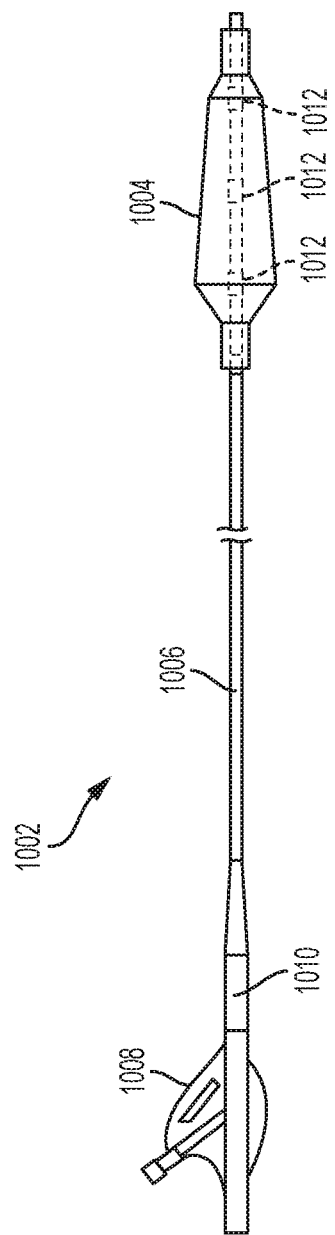
FIG. 10 is a side view of another occlusion balloon device according to embodiments of the present disclosure.

FIG. 10 is a side view of another exemplary occlusion balloon device 1002 device according to embodiments of the present disclosure. The occlusion balloon device 1002 generally includes an inflatable balloon 1004 that is carried at a distal portion of a catheter shaft 1006. The occlusion balloon device 1002 also includes a connection hub 1008 that is carried at a proximal portion of the catheter shaft 1006. The connection hub 1008 and the catheter shaft 1006 may carry a distally-tapering strain relief 1010 at an interface therebetween. The catheter shaft 1006 may also carry one or more radiopaque markers 1012 such that the position of the occlusion balloon device 1002 may be determined via medical imaging (for example, via fluoroscopy). The catheter shaft 1006 may carry, for example, three radiopaque markers 1012 as shown in FIG. 10. A first radiopaque marker 1012 may be axially aligned with a proximal portion of the inflatable balloon 1004, a second radiopaque marker 1012 may be axially aligned with an intermediate portion of the inflatable balloon 1004, and a third radiopaque marker 1012 may be axially aligned with a distal portion of the inflatable balloon 1004.

FIGS. 11A and 11B are a partial longitudinal section view and a front view of the inflatable balloon 1004 of the occlusion balloon device 1002 of FIG. 10, respectively, wherein the inflatable balloon 1004 is depicted in an inflated state. The inflatable balloon 1004 may include a wall 1102, an inflation chamber 1104, a proximal neck 1106 having a length 1110, a distal neck 1124 having a length 1128, a working portion 1116 having a length 1120, a proximal tapered portion 1112 disposed between the proximal neck 1106 and the working portion 1116, and a distal tapered portion 1122 disposed between the distal neck 1124 and the working portion 1116.

The wall 1102 of the inflatable balloon 1004 defines the inflation chamber 1104. The inflation chamber 1104 is adapted to receive an inflation fluid (for example, about 80 percent saline (that is, 80 percent±5 percent) and about 20 percent contrast solution (that is, 20 percent±5 percent)) that inflates the balloon. Upon a clinician introducing the occlusion balloon device 1002 into the vasculature, positioning the inflatable balloon 1004 adjacent the perforation 108 and inflating the inflatable balloon, the inflatable balloon 1004 facilitates occlusion of the perforation 108.

In some embodiments, the inflatable balloon 1004 is formed of one or more relatively compliant materials. Such materials facilitate filling vessels of different diameters, vessels having irregularities, and/or vessels carrying implanted objects (such as cardiac leads) without imparting relatively high dilation forces on a vessel. The inflatable balloon 1004 may be formed of one or more elastomeric materials, such as polyurethane. For example, the inflatable balloon 1004 may be formed of Pellethane®, specifically 80AE Pellethane®, which is available from The Lubrizol Corporation. The inflatable balloon 1004 may have a Shore A durometer of about 85 A (that is, 85 A±4 A).

The proximal neck 1106 engages the catheter shaft 1006 via one or more adhesives, a compression fit, or the like. The proximal neck 1106 may have an inner diameter 1108 of about 2.5 mm (that is, 2.5 mm±0.07 mm). The proximal neck 1106 may have a length 1110 of about 10 mm (that is, 10 mm±1 mm). The proximal neck 1106 may have a wall thickness of about 0.24 mm (that is, 0.24 mm±0.01 mm).

Distal to the proximal neck 1106, the proximal neck 1106 couples to the proximal tapered portion 1112. The proximal tapered portion 1112 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm 0.0064 mm). When the inflatable balloon 1004 is inflated, the proximal tapered portion 1112 may be disposed at an angle 1113 of about 35 degrees (that is, 35 degrees±10 degrees) relative to a longitudinal axis 1114 of the inflatable balloon 1004.

Distal to the proximal tapered portion 1112, the proximal tapered portion 1112 couples to the working portion 1116. The working portion 1116, when the inflatable balloon 1004 is appropriately positioned and inflated, occludes the perforation 108. The working portion 1116 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). The working portion 1116 may have a length 1120 of about 115 mm (that is, 115 mm±3 mm) to about 65 mm (that is, 65 mm±3 mm).

The working portion 1116 tapers inwardly from a first outer diameter 1130 (at the interface with the proximal tapered portion 1112) to a second outer diameter 1132 (at the interface with the distal tapered portion 1122). When inflated, the first outer diameter 1130 may be greater than about 35 mm (that is, 35 mm±2 mm), for example between about 35 mm (that is, 35 mm±2 mm) and about 50 mm (that is, 50 mm±2 mm) and possibly further between about 35 mm (that is, 35 mm±2 mm) and about 45 mm (that is, 45 mm±2 mm). When inflated, the second outer diameter 1132 may be greater than about 16 mm (that is, 16 mm±2 mm), for example between about 16 mm (that is, 16 mm±2 mm) and about 30 mm (that is, 30 mm±2 mm) and possibly further between about 16 mm (that is, 16 mm±2 mm) and about 25 mm (that is, 25 mm±2 mm).

The ratio of the length 1120 of the working portion 1116 to the first outer diameter 1130 of the inflatable balloon 1004 in when inflated is, therefore, about 1.3:1 to about 3.3:1, and the ratio of the length 1120 of the working portion 1116 to the second outer diameter 1132 of the inflatable balloon 1004 in when inflated is, therefore, about 2.2:1 to about 7.2:1. Having these ratios with a relatively long working length provides a balloon that is particularly suitable for occluding perforations at or between the right innominate vein and the top portion of the right atrial chamber. That is, the distal portion of the working portion 1116 is particularly suitable for occluding perforations in the right innominate vein and the proximal portion of the working portion 1116 is particularly suitable for occluding perforations at the top portion of the atrial chamber. More generally, inflating the working portion 1116 to the diameters described above increases the likelihood that the working portion 1116 will be about the same diameter or slightly larger than the diameter of the blood vessel 102 at the perforation 108. Inflating the working portion 1116 to be about the same diameter or slightly larger than the diameter of the blood vessel 102 at the perforation 108 increases the likelihood that the inflatable balloon 1004 will block the perforation 108 without increasing its size.

In some embodiments and as shown in FIGS. 11A and 11B, the working portion may taper inwardly from the first outer diameter 1130 to the second outer diameter 1132 at a constant slope. Stated another way, the working portion 1116 may have a frusto-conical shape. In some embodiments, the working portion may taper inwardly from the first outer diameter 1130 to the second outer diameter 1132 at a non-constant slope.

Again, the inflatable balloon 1004 may be formed of one or more elastomeric materials, such as polyurethane. To inflate the inflatable balloon 1004 to the range of diameters referenced above, it may also be desirable to inflate the inflatable balloon 1004 with an inflation fluid to a pressure within the balloon inflation chamber 1104 from about 0 psi to about 3 psi. The amount of inflation fluid used to inflate the inflatable balloon 1004 to such a pressure and/or at the desired diameter is about 20 ml (cc) to about 60 ml (cc).

Distal to the working portion 1116, the working portion 1116 couples to the distal tapered portion 1122. The distal tapered portion 1122 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1004 is inflated, the distal tapered portion 1122 may be disposed at an angle 1123 of about 30 degrees (that is, 30 degrees±10 degrees) relative to the longitudinal axis 1114.

The distal neck 1124 engages the catheter shaft 1006 via one or more adhesives, a compression fit, or the like. The distal neck 1124 may have an inner diameter 1126 of about 2.5 mm (that is, 2.5 mm±0.07 mm). The distal neck 1124 may have a length 1128 of about 10 mm (that is, 10 mm±1 mm). The distal neck 1124 may have a wall thickness of about 0.24 mm (that is, 0.24 mm±0.01 mm).

The catheter shaft 1006, connection hub 1008, strain relief 1010, and the radiopaque marker(s) 1012 may be similar to the catheter shafts, connection hubs, strain reliefs, and the radiopaque markers, respectively, described above.

Figure 12A:
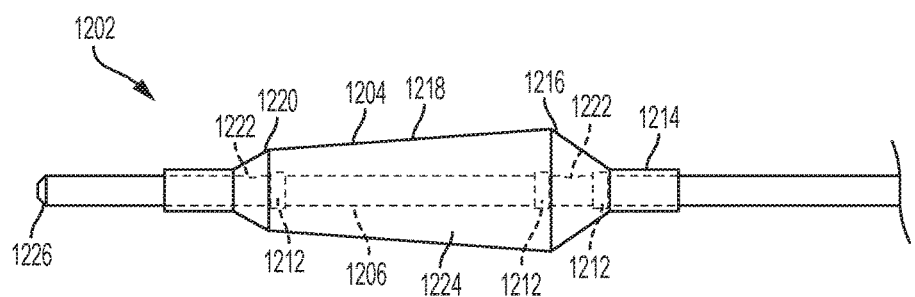
FIG. 12A is a partial side view of an occlusion balloon device according to embodiments of the present disclosure.
Figure 12B:
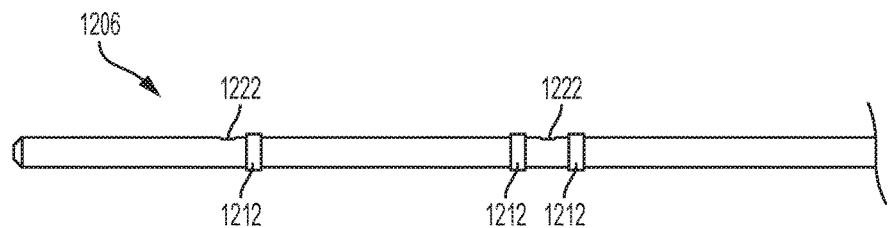
FIG. 12B is a detail view of a catheter shaft of the occlusion balloon device within line 12B-12B of FIG. 12A.

FIGS. 12A and 12B are side views of a distal portion of another exemplary occlusion balloon device 1202 device according to embodiments of the present disclosure. The occlusion balloon device 1202 generally includes an inflatable balloon 1204, which may be similar to the balloon 1004 described above. The inflatable balloon 1204 is carried at a distal portion of a catheter shaft 1206. The occlusion balloon device 1202 also includes a connection hub (not shown), which may be similar to the connection hubs described above. The connection hub is carried at a proximal portion of the catheter shaft 1206. The connection hub and the catheter shaft 1206 may carry a distally-tapering strain relief (not shown), which may be similar to the strain reliefs described above, at an interface therebetween. The catheter shaft 1206 may also carry one or more radiopaque markers 1212 such that the position of the occlusion balloon device 1202 may be determined via medical imaging (for example, via fluoroscopy). The catheter shaft 1206 may carry, for example, three radiopaque markers 1212 as shown in FIGS. 12A and 12B. A first radiopaque marker 1212 may be axially aligned with an intersection of a proximal neck 1214 of the balloon 1204 and a proximal tapered portion 1216 of the balloon 1204. A second radiopaque marker 1212 may be axially aligned with the intersection of the proximal tapered portion 1216 and a working portion 1218 of the balloon 1204. A third radiopaque marker 1212 may be axially aligned with the intersection of the working portion 1218 and a distal tapered portion 1220 of the balloon 1204.

The catheter shaft 1206 may include first and second lumens (not shown) that are similar to the first and second lumens, respectively, described above. The catheter shaft 1206 also includes one or more apertures 1222 that couple the second lumen to the exterior of the catheter shaft 1206 and the balloon inflation chamber 1224. That is, the second lumen delivers the inflation fluid to the inflatable balloon 1204 via one or more apertures 1222. The catheter shaft 1206 may include, for example, two apertures 1222 as shown in FIGS. 12A and 12B. A first aperture 1222 may be axially aligned with the proximal tapered portion 1216 of the balloon 1204. A second aperture 1222 may be axially aligned with the distal tapered portion 1220 of the balloon 1204.

A distal end of the catheter shaft 1206 carries a distal tip 1226 that covers the second lumen of the catheter shaft 1206. The distal tip 1226 includes an opening (not shown) that is aligned with the first lumen of the catheter shaft 1206. Together with the first lumen, the opening is adapted to receive a guidewire or an implanted cardiac lead. The distal tip 1226 may be formed of one or more elastomeric materials, such as polyurethane. For example, the distal tip 1226 may be formed of Pellethane®, specifically 65D Pellethane®, which is available from The Lubrizol Corporation.

A number of variations and modifications to the occlusion balloon devices 1002 and 1202 may be used. For example, if the catheters 1002 or 1202 is to be inserted using a non-femoral vein approach (for example, a jugular vein approach), the working portion may taper inwardly proceeding in a proximal direction.

Figure 13:
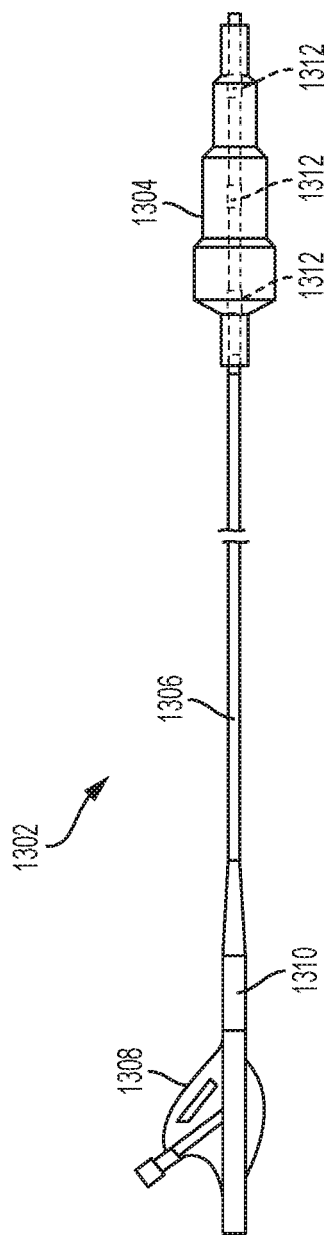
FIG. 13 is a side view of another occlusion balloon device according to embodiments of the present disclosure.

FIG. 13 is a side view of another exemplary occlusion balloon device 1302 device according to embodiments of the present disclosure. The occlusion balloon device 1302 generally includes an inflatable balloon 1304 that is carried at a distal portion of a catheter shaft 1306. The occlusion balloon device 1302 also includes a connection hub 1308 that is carried at a proximal portion of the catheter shaft 1306. The connection hub 1308 and the catheter shaft 1306 may carry a distally-tapering strain relief 1310 at an interface therebetween. The catheter shaft 1306 may also carry one or more radiopaque markers 1312 such that the position of the occlusion balloon device 1302 may be determined via medical imaging (for example, via fluoroscopy). The catheter shaft 1306 may carry, for example, three radiopaque markers 1312 as shown in FIG. 13. A first radiopaque marker 1312 may be axially aligned with a proximal portion of the inflatable balloon 1304, a second radiopaque marker 1312 may be axially aligned with an intermediate portion of the inflatable balloon 1304, and a third radiopaque marker 1312 may be axially aligned with a distal portion of the inflatable balloon 1304.

Figures 14A, 14B:
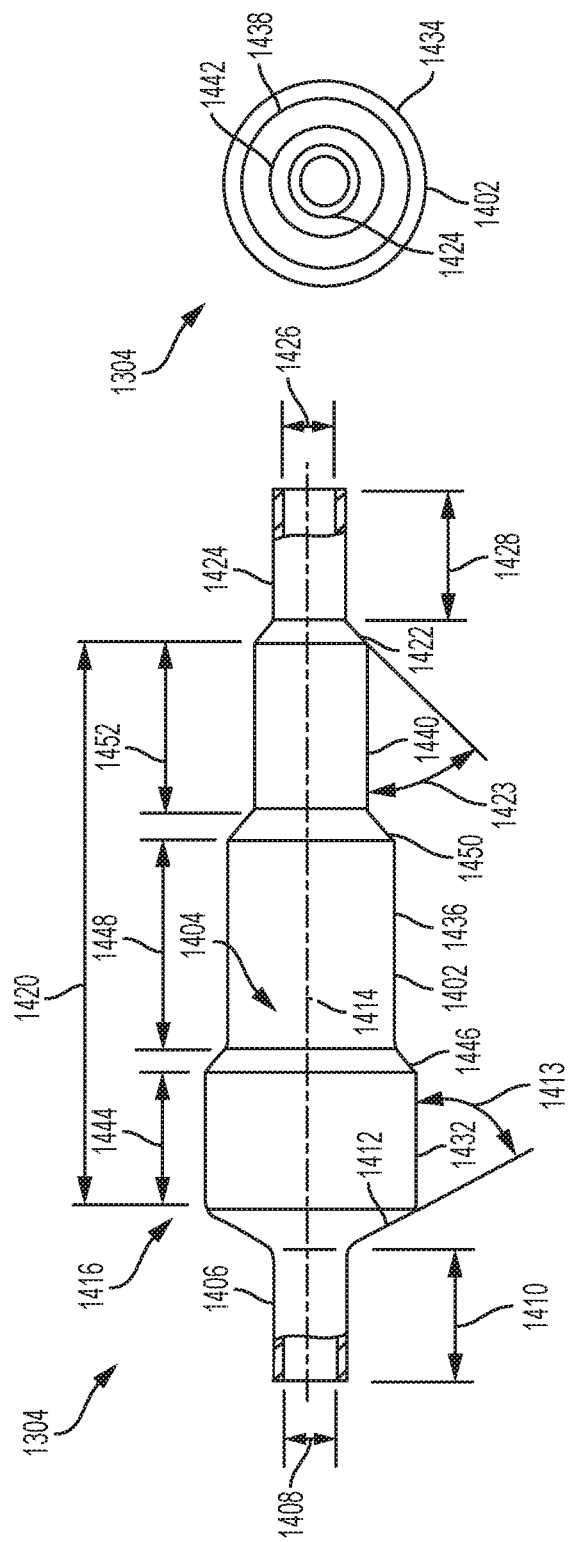
FIG. 14A is a partial longitudinal section view of a balloon of the occlusion balloon device of FIG. 13.
FIG. 14B is a front view of the balloon of FIG. 14A.

FIGS. 14A and 14B are a partial longitudinal section view and a front view of the inflatable balloon 1304 of the occlusion balloon device 1302 of FIG. 13, respectively, wherein the inflatable balloon 1304 is depicted in an inflated state. The inflatable balloon 1304 may include a wall 1402, an inflation chamber 1404, a proximal neck 1406 having a length 1410, a distal neck 1424 having a length 1428, a multiple-diameter working portion 1416 having a length 1420, a proximal tapered portion 1412 disposed between the proximal neck 1406 and the working portion 1416, and a distal tapered portion 1422 disposed between the distal neck 1424 and the working portion 1416.

The wall 1402 of the inflatable balloon 1304 defines the inflation chamber 1404. The inflation chamber 1404 is adapted to receive an inflation fluid (for example, about 80 percent saline (that is, 80 percent±5 percent) and about 20 percent contrast solution (that is, 20 percent±5 percent)) that inflates the balloon. Upon a clinician introducing the occlusion balloon device 1302 into the vasculature, positioning the inflatable balloon 1304 adjacent the perforation 108 and inflating the inflatable balloon, the inflatable balloon 1304 facilitates occlusion of the perforation 108.

In some embodiments, the inflatable balloon 1304 is formed of one or more relatively compliant materials. Such materials facilitate filling vessels of different diameters, vessels having irregularities, and/or vessels carrying implanted objects (such as cardiac leads) without imparting relatively high dilation forces on a vessel. The inflatable balloon 1304 may be formed of one or more elastomeric materials, such as polyurethane. For example, the inflatable balloon 1304 may be formed of Pellethane®, specifically 80AE Pellethane®, which is available from The Lubrizol Corporation. The inflatable balloon 1304 may have a Shore A durometer of about 85 A (that is, 85 A±4 A).

The proximal neck 1406 engages the catheter shaft 1306 via one or more adhesives, a compression fit, or the like. The proximal neck 1406 may have an inner diameter 1408 of about 2.5 mm (that is, 2.5 mm±0.07 mm). The proximal neck 1406 may have a length 1410 of about 10 mm (that is, 10 mm±1 mm). The proximal neck 1406 may have a wall thickness of about 0.24 mm (that is, 0.24 mm±0.01 mm).

Distal to the proximal neck 1406, the proximal neck 1406 couples to the proximal tapered portion 1412. The proximal tapered portion 1412 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1304 is inflated, the proximal tapered portion 1412 may be disposed at an angle 1413 of about 60 degrees (that is, 60 degrees±10 degrees) relative to a longitudinal axis 1414 of the inflatable balloon 1304.

Distal to the proximal tapered portion 1412, the proximal tapered portion 1412 couples to the multiple-diameter working portion 1416. The working portion 1416, when the inflatable balloon 1304 is appropriately positioned and inflated, occludes the perforation 108. The working portion 1416 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). The working portion 1416 may have an overall length 1420 of about 125 mm (that is, 125 mm±3 mm) to about 85 mm (that is, 85 mm±3 mm).

The working portion 1416 includes a plurality of sections that each have a different outer diameter. For example and as shown in the figures, the working portion 1416 may include a proximal or first section 1432 having a first outer diameter 1434, an intermediate or second section 1436 having a second outer diameter 1438, and a distal or third section 1440 having a third outer diameter 1442. The first outer diameter 1434 may be greater than the second outer diameter 1438 and the second outer diameter 1438 may be greater than the third outer diameter 1442.

The first section 1432 may have a length 1444 greater than about 18 mm (that is, 18 mm±2 mm), for example between about 18 mm (that is, 18 mm±2 mm) and about 25 mm (that is, 25 mm±2 mm). When inflated, the first outer diameter 1434 may be between about 60 mm (that is, 60 mm±2 mm) and about 40 mm (that is, 40 mm±2 mm), and possibly about 50 mm (that is, 50 mm±2 mm).

Distal to the first section 1432, a first intermediate tapered portion 1446 couples the first section 1432 to the second section 1436. The first intermediate tapered portion 1446 may be disposed at an angle of about 45 degrees (that is, 45 degrees±10 degrees) relative to the longitudinal axis 1414 of the inflatable balloon 1304.

The second section 1436 may have a length 1448 greater than about 52 mm (that is, 52 mm±2 mm), for example between about 52 mm (that is, 52 mm±2 mm) and about 60 mm (that is, 60 mm±2 mm). When inflated, the second outer diameter 1438 may be between about 30 mm (that is, 30 mm±2 mm) and about 10 mm (that is, 10 mm±2 mm), and possibly about 20 mm (that is, 20 mm±2 mm).

Distal to the second section 1436, a second intermediate tapered portion 1450 couples the second section 1436 to the third section 1440. The second intermediate tapered portion 1450 may be disposed at an angle of about 45 degrees (that is, 45 degrees±10 degrees) relative to the longitudinal axis 1414 of the inflatable balloon 1304.

The third section 1440 may have a length 1452 between about 40 mm (that is, 40 mm±2 mm) and about 20 mm (that is, 20 mm±2 mm), and possibly about 30 mm (that is, 30 mm 2 mm). When inflated, the third outer diameter 1442 may be between about 26 mm (that is, 26 mm±2 mm) and about 6 mm (that is, 6 mm±2 mm), and possibly about 16 mm (that is, 16 mm±2 mm).

The ratio of the overall length 1420 of the working portion 1416 to the first outer diameter 1434 of the inflatable balloon 1304 in when inflated is, therefore, about 1.4:1 to about 3.1:1, ratio of the overall length 1420 of the working portion 1416 to the second outer diameter 1438 of the inflatable balloon 1304 in when inflated is, therefore, about 2.8:1 to about 12.5:1, and the ratio of the length 1420 of the working portion 1416 to the third outer diameter 1442 of the inflatable balloon 1304 in when inflated is, therefore, about 3.3:1 to about 20.8:1. Having these ratios with a relatively long working length provides a balloon that is particularly suitable for occluding perforations at or between the right innominate vein and the top portion of the right atrial chamber. That is, the third section 1440 of the working portion 1416 is particularly suitable for occluding perforations in the right innominate vein, the second section 1436 of the working portion 1416 is particularly suitable for occluding perforations in the superior vena cava, and the first section 1432 of the working portion 1416 is particularly suitable for occluding perforations at the top portion of the atrial chamber. More generally, inflating the working portion 1416 to the diameters described above increases the likelihood that the working portion 1416 will be about the same diameter or slightly larger than the diameter of the blood vessel 102 at the perforation 108. Inflating the working portion 1416 to be about the same diameter or slightly larger than the diameter of the blood vessel 102 at the perforation 108 increases the likelihood that the inflatable balloon 1304 will block the perforation 108 without increasing its size.

In some embodiments, the first section 1432 of the working portion 1416 inhibits blood flowing from the inferior vena cava from exiting through a perforation at the junction of the superior vena cava and the right atrium. That is, the first section 1432 of the working portion 1416 may act as a plug or baffle that redirects flow into the ventricle.

Again, the inflatable balloon 1304 may be formed of one or more elastomeric materials, such as polyurethane. To inflate the inflatable balloon 1304 to the range of diameters referenced above, it may also be desirable to inflate the inflatable balloon 1304 with an inflation fluid to a pressure within the balloon inflation chamber 1404 from about 0 psi to about 3 psi. The amount of inflation fluid used to inflate the inflatable balloon 1304 to such a pressure and/or at the desired diameter is about 20 ml (cc) to about 60 ml (cc).

Distal to the working portion 1416, the working portion 1416 couples to the distal tapered portion 1422. The distal tapered portion 1422 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1304 is inflated, the distal tapered portion 1422 may be disposed at an angle 1423 of about 45 degrees (that is, 45 degrees±10 degrees) relative to the longitudinal axis 1414.

The distal neck 1424 engages the catheter shaft 1306 via one or more adhesives, a compression fit, or the like. The distal neck 1424 may have an inner diameter 1426 of about 2.5 mm (that is, 2.5 mm±0.07 mm). The distal neck 1424 may have a length 1428 of about 10 mm (that is, 10 mm±1 mm). The distal neck 1424 may have a wall thickness of about 0.24 mm (that is, 0.24 mm±0.01 mm).

The catheter shaft 1306, connection hub 1308, strain relief 1310, and the radiopaque marker(s) 1312 may be similar to the catheter shafts, connection hubs, strain reliefs, and the radiopaque markers, respectively, described above.

Figure 15A:
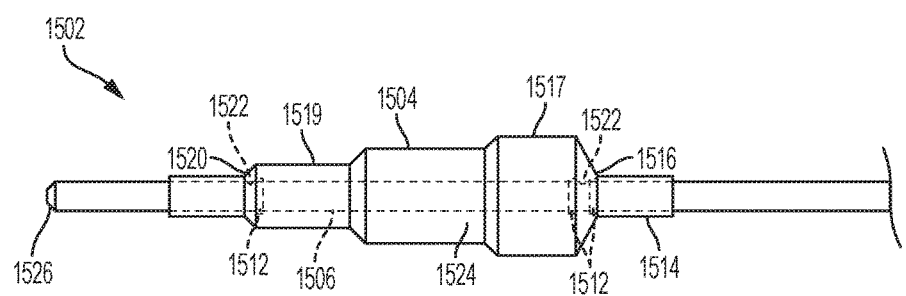
FIG. 15A is a partial side view of an occlusion balloon device according to embodiments of the present disclosure.
Figure 15B:
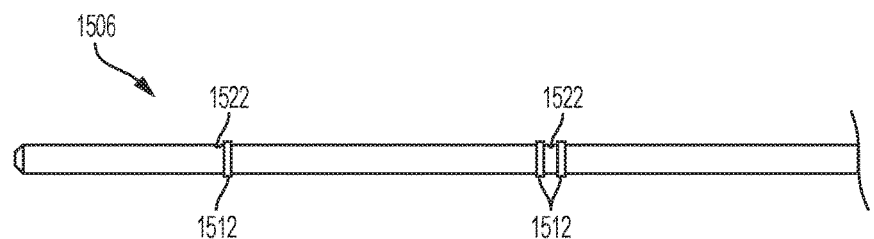
FIG. 15B is a detail view of a catheter shaft of the occlusion balloon device within line 15B-15B of FIG. 15A.

FIGS. 15A and 15B are side views of a distal portion of another exemplary occlusion balloon device 1502 device according to embodiments of the present disclosure. The occlusion balloon device 1502 generally includes an inflatable balloon 1504, which may be similar to the balloon 1304 described above. The inflatable balloon 1504 is carried at a distal portion of a catheter shaft 1506. The occlusion balloon device 1502 also includes a connection hub (not shown), which may be similar to the connection hubs described above. The connection hub is carried at a proximal portion of the catheter shaft 1506. The connection hub and the catheter shaft 1506 may carry a distally-tapering strain relief (not shown), which may be similar to the strain reliefs described above, at an interface therebetween. The catheter shaft 1506 may also carry one or more radiopaque markers 1512 such that the position of the occlusion balloon device 1502 may be determined via medical imaging (for example, via fluoroscopy). The catheter shaft 1506 may carry, for example, three radiopaque markers 1512 as shown in FIGS. 15A and 15B. A first radiopaque marker 1512 may be axially aligned with an intersection of a proximal neck 1514 of the balloon 1504 and a proximal tapered portion 1516 of the balloon 1504. A second radiopaque marker 1512 may be axially aligned with the intersection of the proximal tapered portion 1516 and a proximal section 1517 of a working portion of the balloon 1504. A third radiopaque marker 1512 may be axially aligned with the intersection of a distal section 1519 of the working portion and a distal tapered portion 1520 of the balloon 1504.

The catheter shaft 1506 may include first and second lumens (not shown) that are similar to the first and second lumens, respectively, described above. The catheter shaft 1506 also includes one or more apertures 1522 that couple the second lumen to the exterior of the catheter shaft 1506 and the balloon inflation chamber 1524. That is, the second lumen delivers the inflation fluid to the inflatable balloon 1504 via one or more apertures 1522. The catheter shaft 1506 may include, for example, two apertures 1522 as shown in FIGS. 15A and 15B. A first aperture 1522 may be axially aligned with the proximal tapered portion 1516 of the balloon 1504. A second aperture 1522 may be axially aligned with the distal tapered portion 1520 of the balloon 1504.

A distal end of the catheter shaft 1506 carries a distal tip 1526 that covers the second lumen of the catheter shaft 1506. The distal tip 1526 includes an opening (not shown) that is aligned with the first lumen of the catheter shaft 1506. Together with the first lumen, the opening is adapted to receive a guidewire or an implanted cardiac lead. The distal tip 1526 may be formed of one or more elastomeric materials, such as polyurethane. For example, the distal tip 1526 may be formed of Pellethane®, specifically 65D Pellethane®, which is available from The Lubrizol Corporation.

Figure 16A:
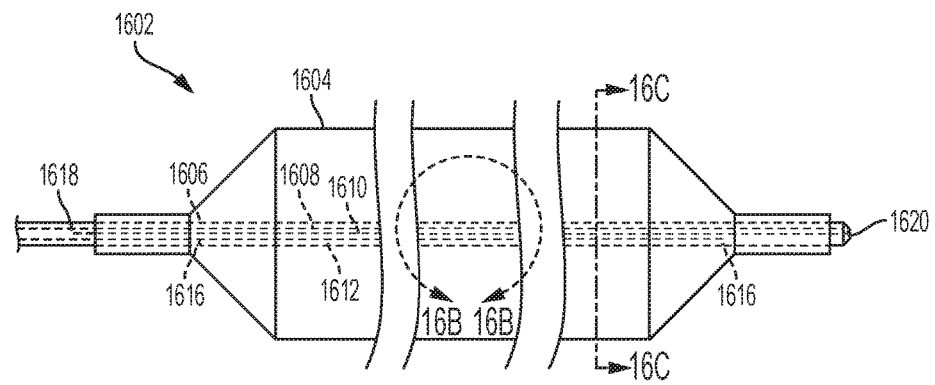
FIG. 16A is a side view of an occlusion balloon device according to embodiments of the present disclosure.
Figure 16B:
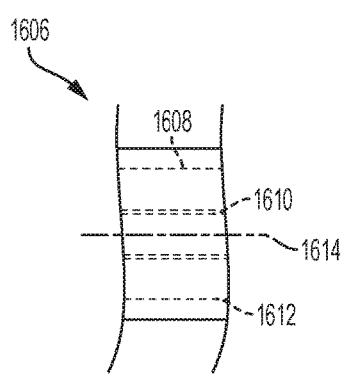
FIG. 16B is a detail view of a catheter shaft of the occlusion balloon device within line 16B-16B of FIG. 16A.
Figure 16C:
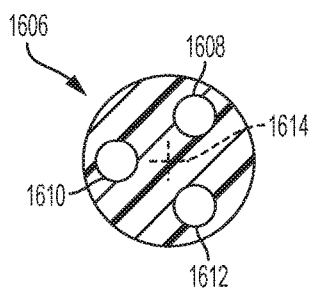
FIG. 16C is a cross-sectional view of the catheter shaft of the occlusion balloon device along line 16C-16C of FIG. 16A.

FIGS. 16A and 16B are views of a distal portion of another exemplary occlusion balloon device 1602 device according to embodiments of the present disclosure. The occlusion balloon device 1602 generally includes an inflatable balloon 1604, which may be similar to any of the balloons described herein. The inflatable balloon 1604 is carried at a distal portion of a catheter shaft 1606. The occlusion balloon device 1602 also includes a connection hub (not shown), which may be similar to the connection hubs described above. The connection hub is carried at a proximal portion of the catheter shaft 1606. The connection hub and the catheter shaft 1606 may carry a distally-tapering strain relief (not shown), which may be similar to the strain reliefs described above, at an interface therebetween.

The catheter shaft 1606 includes a first lumen 1608, a second lumen 1610, and a third lumen 1612. The lumens 1608, 1610, and 1612 may be disposed about the longitudinal axis 1614 of the catheter shaft 1606 at equal angles, although other arrangements are also contemplated. The first lumen 1604 is adapted to receive a guidewire or an implanted cardiac lead to guide the occlusion balloon device 1602 to a position proximate the perforation 108. The second lumen 1610 delivers inflation fluid to the inflatable balloon 1604 via one or more apertures 1616. The catheter shaft 1606 may include, for example, two apertures 1616 as shown in FIG. 16A. The third lumen 1612 acts as a blood perfusion lumen. That is, the third lumen 1612 facilitates passage of blood through the catheter shaft 1606 and from one end of the inflatable balloon 1604 to the other. The third lumen 1612 is coupled to a first aperture 1618 disposed proximally of the balloon device 1602 and a second aperture 1620 disposed distally of the balloon device 1602. The first aperture 1618 may be disposed on the side of the catheter shaft 1606. The second aperture 1620 may be disposed on the distal end of the catheter shaft 1606.

The catheter shaft 1606 may carry one or more radiopaque markers (not shown) in any of the manners described herein.

FIGS. 17A and 17B are views of a distal portion of another exemplary occlusion balloon device 1702 device according to embodiments of the present disclosure. The occlusion balloon device 1702 generally includes an inflatable balloon 1704, which may be similar to any of the balloons described herein. The inflatable balloon 1704 is carried at a distal portion of a catheter shaft 1706, which may be similar to any of the catheter shafts described herein. The occlusion balloon device 1702 also includes a connection hub (not shown), which may be similar to the connection hubs described above. The connection hub is carried at a proximal portion of the catheter shaft 1706. The connection hub and the catheter shaft 1706 may carry a distally-tapering strain relief (not shown), which may be similar to the strain reliefs described above, at an interface therebetween.

The occlusion balloon device 1702 also includes an occlusion patch 1708 that is detachably carried on the outer surface of the working portion 1710 of the inflatable balloon 1704. The inflatable balloon 1704 may deploy the occlusion patch 1708 (for example, by inflation of the balloon 1704) to position the patch 1708 over a vascular perforation and thereby occlude the perforation. In some embodiments, occlusion patch 1708 may include one or more adhesives to maintain the position of the patch 1708 within the vasculature. The adhesive properties of the one or more adhesives may be activated in various manners, such as through the application of one or more of heat, pH, light, and the like. In some embodiments, the adhesives may be activated by the application of ultraviolet light. For example, adhesive compositions of the present disclosure may be activated as described in "A Blood-Resistant Surgical Glue for Minimally Invasive Repair of Vessels and Heart Defects," Lang et al., *Science Translational Medicine*, Vol. 6, Issue 218, Jan. 8, 2014; "A Light-Reflecting Balloon Catheter for Atraumatic Tissue Defect Repair," Roche et al., *Science Translational Medicine*, Vol. 7, Issue 306, Sep. 23, 2015; and WO 2015/175662, which are hereby incorporated herein by reference in their entirety for all that they teach and for all purposes.

In some embodiments, the adhesive may comprise adhesives currently used in clinical settings, including, but not limited to, cyanoacrylates, bovine serum albumin (BSA)-glutaraldehyde, fibrin sealants, gelatin matrix thrombin, gelatin sponge, oxidized cellulose, collagen sponge, collagen fleece, recombinant factor VIIa, and the like. In some embodiments, the adhesive may comprise hydrophobic functional groups, such as hexanoyl (Hx; C6), palmitoyl (Pam; C16), stearoyl (Ste; C18), and oleoyl (Ole; C18 unsaturated) groups, so as to resist being washed out or disengaged from their substrate in predominately aqueous environments (e.g., vascular tissue). Such adhesives include, but are not limited to, 10Ole-disuccinimidyl tartrate, 10Ste-disuccinimidyl, and variations and combinations thereof.

Adhesives may be combined with various other compounds to facilitate their attachment to the occlusion patch 1708. For example, adhesives may be combined with various compounds (e.g., solubilizing agents) that aid in the generation of a solution or mixture comprising the adhesive, which can be used to coat the occlusion patch 1708.

In some embodiments, a biodegradable and biocompatible hydrophobic polymer may be used as the adhesive. For example, the biodegradable and biocompatible hydrophobic polymer may be poly(glycerol sebacate acrylate) (PGSA), or variations and combinations thereof, which can be cross-linked using UV light. Ultraviolet light may be emitted from the distal end of an ultraviolet light-emitting catheter, which may be disposed within or outside of the inflatable balloon 1704, to activate the PGSA attached to the occlusion patch 1708. If the ultraviolet light-emitting catheter is disposed within the balloon 1704, the ultraviolet light-emitting catheter may be disposed (partially or entirely) within the portion of the catheter shaft 1706 that is within the balloon 1704 or the ultraviolet light-emitting catheter may be disposed between the catheter shaft 1706 and the interior side of the balloon 1704. The wall of the inflatable balloon 1704 may be translucent to facilitate transmission of the ultraviolet light from the ultraviolet light-emitting catheter to the occlusion patch 1708.

In some embodiments, the patch 1708 may be constructed of bovine pericardium, porcine small intestine submucosa, polyethylene terephthalate and Poly(glycerol sebacate urethane) (PGSU). Additionally, the patch 1708 may include a scaffold structure 1712 to facilitate tissue growth therein. In some embodiments, the patch 1708 includes stem cells to facilitate bioabsorption of the patch 1708. In some embodiments, the patch 1708 includes one or more hormonal agents, such as growth factors to promote wound healing and other therapeutic agents. In a specific embodiment, a hormonal agent may be delivered via a delivery vehicle, such as a nanoparticle or microparticle.

The occlusion patch 1708 may include any of various dimensions. In some embodiments and as shown in FIG. 17A, the occlusion patch 1708 extends over substantially the entire length of the working portion 1710 of the inflatable balloon 1704. In some embodiments, the occlusion patch 1708 extends over only a portion of the length of the working portion 1710 of the inflatable balloon 1704. In some embodiments and as shown in FIG. 17B, the occlusion patch 1708 extends over only a portion of the circumference of the working portion 1710 of the inflatable balloon 1704. In some embodiments, the occlusion patch 1708 extends over substantially the entire circumference of the working portion 1710 of the inflatable balloon 1704.

Although FIGS. 17A and 17B only illustrate a single occlusion patch 1708, in some embodiments the inflatable balloon 1704 carries a plurality of occlusion patches 1708. The patches 1708 may be offset from each other along the length and/or about the circumference of the working portion 1710 of the inflatable balloon 1704.

A number of variations and modifications to the occlusion balloon devices 1302 and 1502 may be used. For example, if the catheters 1302 or 1502 is to be inserted using a non-femoral vein approach (for example, a jugular vein approach), the working portion may have a distal section with a relatively large diameter and a proximal section with a relatively small diameter. As another example, a perfusion lumen could be formed as part of a balloon device instead of the catheter shaft.

Figure 18:
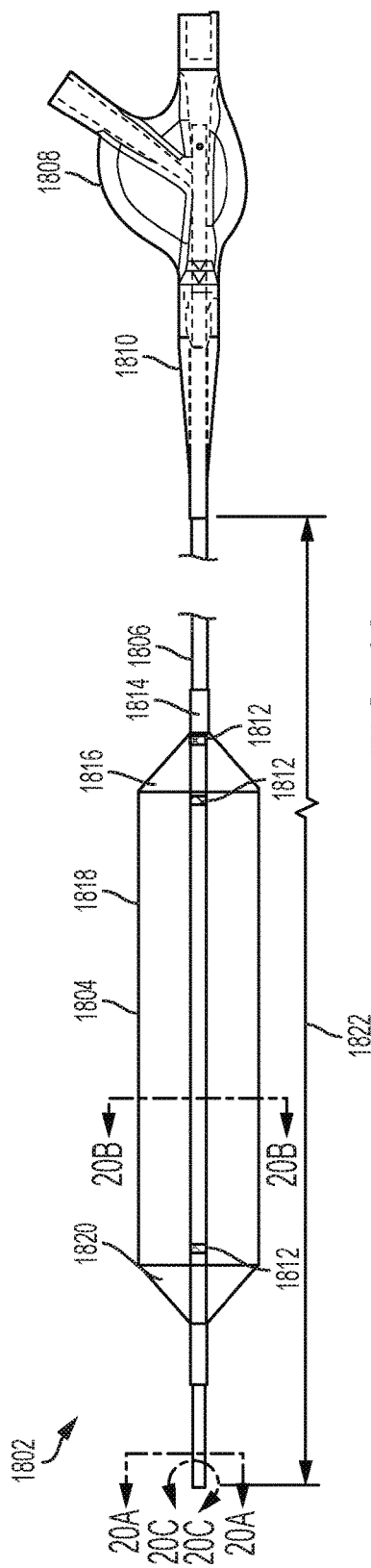
FIG. 18 is a side view of an occlusion balloon device according to embodiments of the present disclosure.

FIG. 18 is a side view of an exemplary occlusion balloon device 1802 device according to embodiments of the present disclosure. The occlusion balloon device 1802 generally includes an inflatable balloon 1804 that is carried at a distal portion of a catheter shaft 1806. The occlusion balloon device 1802 also includes a connection hub 1808 that is carried at a proximal portion of the catheter shaft 1806. The connection hub 1808 and the catheter shaft 1806 may carry a distally-tapering strain relief 1810 at an interface therebetween. The catheter shaft 1806 also carries three radiopaque markers 1812 such that the position of the occlusion balloon device 1802 may be determined via medical imaging (for example, via fluoroscopy). A first radiopaque marker 1812 may be axially near an intersection of a proximal neck 1814 of the balloon 1804 and a proximal tapered portion 1816 of the balloon 1804. A second radiopaque marker 1812 may be axially near an intersection of the proximal tapered portion 1816 and a working portion 1818 of the balloon 1804. A third radiopaque marker 1812 may be axially near an intersection of the working portion 1818 and a distal tapered portion 1820 of the balloon 1804. The device 1802 has an effective length 1822 (that is, a length between the distal end of the strain relief 1810 and the distal end of the shaft 1806) of about 88 cm (that is, 88 cm±1 cm). The device 1802 has a maximum outer diameter, or crossing profile, of about 4 mm (that is, 4 mm±0.1 mm)

Figure 19:
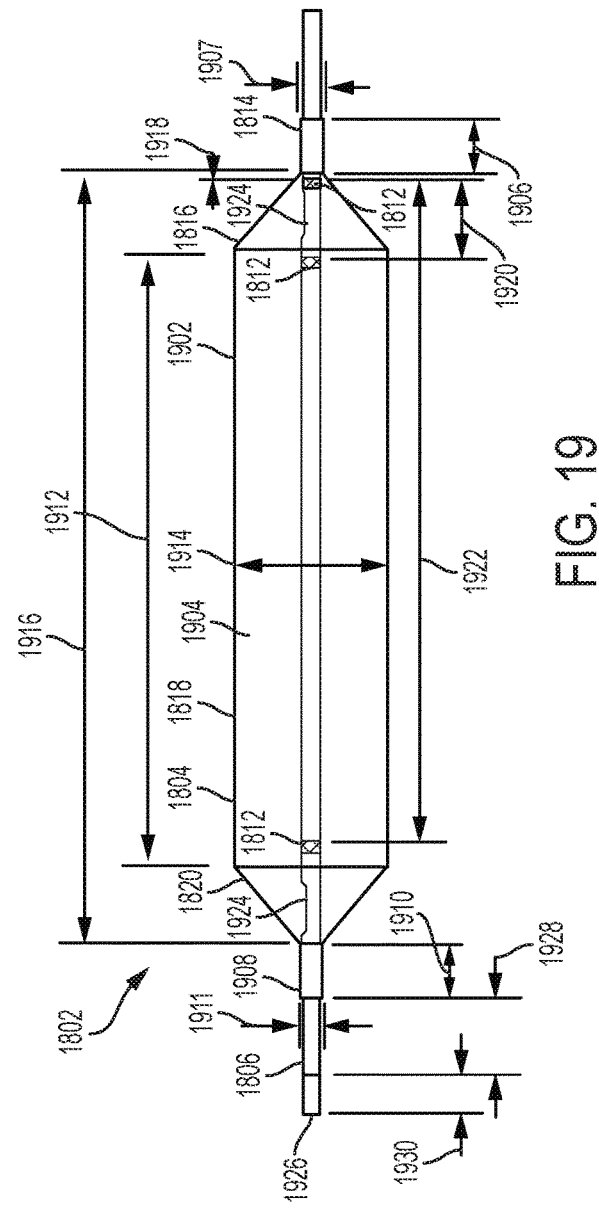
FIG. 19 is a side view of a distal portion of the occlusion balloon device of FIG. 18.

FIG. 19 is a side view of a distal portion of the occlusion balloon device 1802 of FIG. 18, wherein the inflatable balloon 1804 is depicted in an inflated state. The inflatable balloon 1804 includes a wall 1902, an inflation chamber 1904, the proximal neck 1814 (which has a length 1906 and an outer diameter 1907), a distal neck 1908 having a length 1910 and an outer diameter 1911, the working portion 1818 (which has a length 1912), the proximal tapered portion 1816 disposed between the proximal neck 1814 and the working portion 1818, and the distal tapered portion 1820 disposed between the distal neck 1908 and the working portion 1818.

The wall 1902 of the inflatable balloon 1804 defines the inflation chamber 1904. The inflation chamber 1904 is adapted to receive an inflation fluid (for example, about 80 percent saline (that is, 80 percent±5 percent) and about 20 percent contrast solution (that is, 20 percent±5 percent)) that inflates the balloon. Upon a clinician introducing the lead removal catheter 104 into the vasculature, positioning the inflatable balloon 1804 adjacent the perforation 108 and inflating the inflatable balloon, the inflatable balloon 1804 facilitates occlusion of the perforation 108.

In some embodiments, the inflatable balloon 1804 is formed of one or more relatively compliant materials. Such materials facilitate filling vessels of different diameters, vessels having irregularities, and/or vessels carrying implanted objects (such as cardiac leads) without imparting relatively high dilation forces on a vessel. The inflatable balloon 1804 may be formed of one or more elastomeric materials, such as polyurethane. For example, the inflatable balloon 1804 may be formed of Pellethane®, specifically 80AE Pellethane®, which is available from The Lubrizol Corporation of Wickliffe, Ohio. The inflatable balloon 1804 may have a Shore A durometer of about 85 A (that is, 85 A±4 A).

The inflatable balloon 1804 includes the proximal neck 1814, which engages the catheter shaft 1806 (via one or more adhesives, a compression fit, or the like). The proximal neck 1814 may have an inner diameter of about 2.5 mm (that is, 2.5 mm±0.07 mm). The proximal neck 1814 may have a length 1906 of about 10 mm (that is, 10 mm±2 mm). The proximal neck 1814 may have an outer diameter 1907 of about 3.0 mm (that is, 3.0 mm±0.1 mm). The proximal neck 1814 may have a wall thickness of about 0.24 mm (that is, 0.24 mm±0.01 mm).

Distal to the proximal neck 1814, the proximal neck 1814 couples to the proximal tapered portion 1816. The proximal tapered portion 1816 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1804 is inflated, the proximal tapered portion 1816 may be disposed at an angle of about 45 degrees (that is, 45 degrees±0.5') relative to a longitudinal axis of the inflatable balloon 1804.

Distal to the proximal tapered portion 1816, the proximal tapered portion 1816 couples to the working portion 1818. The working portion 1818, when the inflatable balloon 1804 is appropriately positioned and inflated, occludes the perforation 108. The working portion 1818 may have an inflated outer diameter 1914 of about 20 mm (that is, 20 mm±2 mm). The working portion 1818 may have a length 1912 of about 80 mm (that is, 80 mm±3 mm). The working portion 1818 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). The ratio of the length 1912 of the working portion 1818 to the outer diameter 1914 of the inflatable balloon 1804 in the inflated state is, therefore, about 4:1. Having this ratio with a relatively constant inflated outer diameter 1914 of about 20 mm for a length 1912 of about 80 mm increases the likelihood that the inflatable balloon 1804 will occlude the perforation 108 when placed adjacent the perforation 108 in the patient vasculature and inflated. That is, the length 1912 of the working portion 1818 of the inflatable balloon 1804 is designed to be substantially longer than the perforation 108, thereby potentially increasing the clinician's ability to quickly locate and occlude the perforation.

As mentioned above, the working portion 1818 of the inflatable balloon 1804 may have an inflated outer diameter 1914 of about 20 mm (that is, 20 mm±2 mm). Inflating the outer diameter 1914 of the working portion 1818 of the inflatable balloon 1804 to this diameter increases the likelihood that the working portion 1818 of the inflatable balloon 1804 will be about the same diameter or slightly larger than the diameter of the blood vessel 102 at the perforation 108. Inflating the outer diameter 1914 of the working portion 1818 of the inflatable balloon 1804 to be about the same diameter or slightly larger than the diameter of the blood vessel 102 at the perforation 108 increases the likelihood that the inflatable balloon 1804 will block the perforation 108 without increasing its size.

Again, the inflatable balloon 1804 may be formed of one or more elastomeric materials, such as polyurethane. To inflate the inflatable balloon 1804 to the diameter referenced above, it may also be desirable to inflate the inflatable balloon 1804 with an inflation fluid to a pressure within the balloon inflation chamber 1904 from about 0 psi to about 3 psi. The amount of inflation fluid used to inflate the inflatable balloon 1804 to such a pressure and/or at the desired diameter is about 25 ml (cc). Furthermore, the elastomeric material may provide the inflatable balloon 1804 with the compliance characteristics shown in Table 1. That is, providing the inflatable balloon 1804 with a specific volume of inflation fluid may cause the balloon 1804 to inflate to a specific diameter as shown in Table 1.

TABLE 1

Exemplary compliance characteristics of the inflatable balloon 1804.

| Inflation Volume (ml, cc) | Balloon Diameter (mm) |
| --- | --- |
| 20 | 18.8 |
| 25 | 19.4 |
| 30 | 21.3 |
| 35 | 23.4 |
| 40 | 25.2 |
| 45 | 26.9 |
| 50 | 28.6 |
| 55 | 29.9 |
| 60 | 31.1 |

Distal to the working portion 1818, the working portion 1818 couples to the distal tapered portion 1820. The distal tapered portion 1820 may have a wall thickness of about 0.036 mm (that is, 0.036 mm±0.0064 mm), about 0.041 mm (that is, 0.041 mm±0.0064 mm), about 0.046 mm (that is, 0.046 mm±0.0064 mm), or about 0.051 mm (that is, 0.051 mm±0.0064 mm). When the inflatable balloon 1804 is inflated, the distal tapered portion 1820 may be disposed at an angle of about 45 degrees (that is, 45 degrees±0.5') relative to the longitudinal axis of the inflatable balloon 1804.

Distal to the distal tapered portion 1820, the distal tapered portion 1820 couples to the distal neck 1908, which engages the catheter shaft 1806 (via one or more adhesives, a compression fit, or the like). The distal neck 1908 may have an inner diameter of about 2.5 mm (that is, 2.5 mm±0.07 mm). The distal neck 1908 may have a length 1910 of about 10 mm (that is, 10 mm±2 mm). The distal neck 1908 may have an outer diameter 1911 of about 3.0 mm (that is, 3.0 mm±0.1 mm). The distal neck 1908 may have a wall thickness of about 0.24 mm (that is, 0.24 mm±0.01 mm).

Between the distal neck 1908 and the proximal neck 1814, the inflatable balloon 1804 may have a length 1916 of about 100 mm (that is, 100 mm±1 mm).

The first radiopaque marker 1812 may be offset from the intersection of the proximal neck 1814 and a proximal tapered portion 1816 by a distance 1918 of about 1 mm (that is, 1 mm±1 mm). The second radiopaque marker 1812 may be offset from the first radiopaque marker 1812 by a distance 1920 of about 10.27 mm (that is, 10.27 mm±1 mm). The third radiopaque marker 1812 may be offset from the first radiopaque marker 1812 by a distance 1922 of about 86 mm (that is, 86 mm±1 mm).

FIGS. 20A-20D are views of the catheter shaft 1806. The catheter shaft 1806 may be formed of one or more elastomeric materials, such as polyurethane. For example, the catheter shaft 1806 may be formed of Pellethane®, specifically 75D Pellethane®, which is available from The Lubrizol Corporation.

The catheter shaft 1806 may have an outer diameter 2002 of about 2.286 mm (that is, 2.286 mm±0.04 mm). The catheter shaft 1806 may have a length of about 110 cm (that is, 110 cm±0.3 cm).

The catheter shaft 1806 includes a first lumen 2004 that is adapted to receive a guidewire or an implanted cardiac lead to guide the occlusion balloon device 1802 to a position proximate the perforation 108. The first lumen 2004 is non-centrically disposed relative to the outer diameter 2002 of the catheter shaft 1806. Assuming that the first lumen 2004 is adapted to receive a guidewire having a diameter of about 0.9 mm (0.035 inches), the first lumen 2004 may have circular cross section and have a diameter of about 0.954 mm (that is, 0.954 mm±0.04 mm). If, however, the first lumen 2004 is adapted to receive an implanted cardiac lead, the first lumen 2004 may have a different cross section diameter. Also, although the first lumen 2004 is depicted as having a circular cross section, the cross-sectional shape of the first lumen 2004 may have a non-circular section, such as an oval. A minimum wall thickness between the first lumen 2004 and the outer diameter 2002 may be about 0.15 mm (that is, 0.15 mm±0.025 mm).

The catheter shaft 1806 also includes a second lumen 2006 that is adapted to receive the inflation fluid from the connection hub 1808 and deliver the inflation fluid to the balloon inflation chamber 1904. The second lumen 2006 is non-centrically disposed relative to the first lumen 2004 and the outer diameter 2002 of the catheter shaft 1806. The second lumen 2006 may have a circular cross section or a non-circular cross-sectional shape, such as a crescent-like cross-sectional shape or a semi-circular shape. Assuming that the second lumen 2006 has a crescent-like cross-sectional shape or a semi-circular shape, the second lumen 2006 may have a width of about 1.8 mm (that is, 1.8 mm±0.025 mm). The second lumen 2006 may have a height in a plane that bisects the catheter shaft 1806 of about 0.76 mm (that is, 0.76 mm±0.025 mm). It is desirable to introduce as much inflation fluid through the second lumen 2006 and into the inflation chamber of the inflatable balloon as quickly as possible, in order to inflate the inflatable balloon as quickly as possible and minimize potential blood loss through the perforation. Accordingly, it is desirable to have as large as possible a cross-sectional area for the second lumen 2006 for a given outer diameter 2002 of the catheter shaft 1806. For example, for an outer diameter 2002 of about 2.286 mm (that is, 2.286 mm±0.04 mm), the cross-sectional area for the second lumen 2006 may be between 0.65 mm$^2$ and 1.90 mm$^2$ or any increment of 0.01 mm$^2$ therebetween, such as 0.66, 0.67, 0.68, 0.69, 0.70 . . . 1.0 . . . 1.5 . . . 1.9 mm$^2$.

A minimum wall thickness between the second lumen 2006 and the first lumen 2004 may be about 0.1 mm (that is, 0.1 mm±0.025 mm). A minimum wall thickness between the second lumen 2006 and the outer diameter 2002 may be about 0.15 mm (that is, 0.15 mm±0.025 mm). Assuming a minimum thickness between the second lumen 2006 and the outer diameter 2002 is about 0.15 mm, a radius for the crescent-like cross-sectional shape or a semi-circular shape of about 1 mm correlates to a cross-sectional area of the lumen 2006 of between about 1.4 mm$^2$ and 1.7 mm$^2$, and depending upon the wall thickness between the second lumen 2006 and the first lumen 2004, the radius for the crescent-like cross-sectional shape or a semi-circular shape of about 1 mm correlates to a cross-sectional area of the lumen 2006 of between about 1.50 mm$^2$ and 1.60 mm$^2$, and about 1.55 mm$^2$. The crescent-like cross-sectional shape or a semi-circular shape may alternatively have a radius of about between 0.50 mm to 1.50 mm.

Figure 20A:
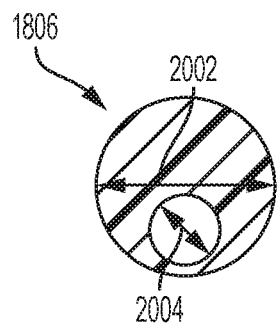
FIG. 20A is a cross-sectional view of a catheter shaft of the occlusion balloon device along line 20A-20A of FIG. 18.
Figure 20B:
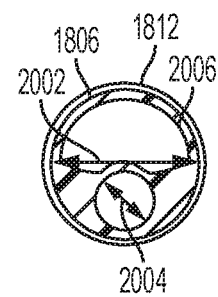
FIG. 20B is a cross-sectional view of the catheter shaft of the occlusion balloon device along line 20B-20B of FIG. 18.
Figure 20C:
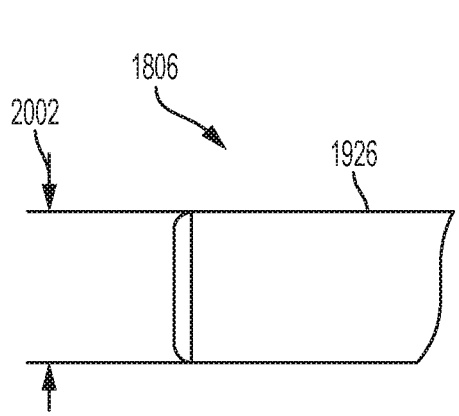
FIG. 20C is a detail view of the catheter shaft of the occlusion balloon device within line 20C-20C of FIG. 18.
Figure 20D:
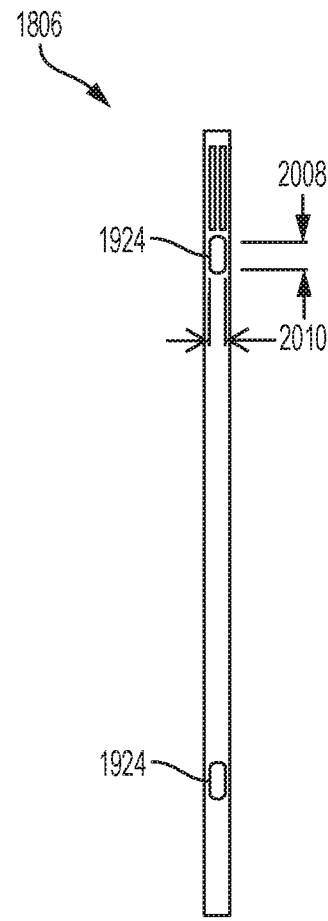
FIG. 20D is a top view of a distal portion of the catheter shaft of the occlusion balloon device of FIG. 18.

The catheter shaft 1806 also includes two apertures 1924 that couple the second lumen 2006 to the exterior of the catheter shaft 1806 and the balloon inflation chamber 1904. That is, the second lumen 2006 delivers the inflation fluid to the inflatable balloon 1804 via the apertures 1924. Referring briefly to FIG. 19, a first aperture 1924 may be axially aligned with the proximal tapered portion 1816 of the balloon 1804 and a second aperture 1924 may be axially aligned with the distal tapered portion 1820 of the balloon 1804. Referring specifically to FIG. 20D, each aperture 1924 may have an axial length 2008 of about 5 mm (that is, 5 mm±1 mm) and a transverse width 2010 of about 1.8 mm (that is, 1.8 mm±0.3 mm). The second lumen 2006 may be covered at the distal end of the catheter shaft 1806 (for example, by a separate cover 1926, the wall of the catheter shaft 1806, or the like). If the catheter shaft 1806 includes a separate cover 1926, the cover 1926 may be offset from the distal neck 1908 by a distance 1928 of about 10 mm (that is, 10 mm±2 mm). The cover 1926 may have an axial length 1930 about 5 mm (that is, 5 mm±2 mm). The catheter shaft 1806 may also include a third aperture (not shown) disposed within the connection hub 1808 to facilitate receiving the inflation fluid from a lumen of the connection hub 1808.

In some embodiments, the dimensions and material properties of the inflatable balloon 1804, the catheter shaft 1806, and the catheter shaft 1806 facilitate using the occlusion balloon device 1802 with relatively small guidewires and introducer sheaths and relatively quickly delivering the inflation fluid to the inflatable balloon 1804 (for example, in 40 seconds or less). Having two or more of the following allows the clinician to quickly inflate the inflatable balloon 1804 with the inflation fluid: a crescent-like cross-sectional shape for the second lumen 2006; a wall thickness between the first lumen 2004 and the outer diameter 2002 about 0.15 mm; a wall thickness between the second lumen 2006 and the outer diameter 2002 about 0.15 mm; wall thickness between the second lumen 2006 and the first lumen 2004 about 0.1 mm; and the apertures 1924 having an axial length 2008 of about 5 mm and a transverse width 2010 of about 1.8 mm, one aperture 1924 being axially aligned with the proximal tapered portion 1816, and the other aperture 1924 being axially aligned distal tapered portion 1820. Testing has demonstrated that occlusion balloon devices having such properties can receive 60 ml of inflation fluid (being 80 percent saline and 20 percent contrast solution) in an average time of 25.6 seconds with a standard deviation of 1.3 seconds to facilitate inflation of the occlusion balloon to a diameter of 31.1 mm. Furthermore, the occlusion balloon device 1802 has sufficient strength for entering a subject's vasculature and occluding a vascular perforation.

The radiopaque markers 1812 may be similar to the radiopaque marker bands 602 described above. The radiopaque markers 1812 may be formed of one or more radiopaque materials, such a mixture of about 90 percent platinum (that is, 90 percent±1 percent) and 10 percent iridium (that is, 10 percent±1 percent). The radiopaque markers 1812 may have an open-ended cylindrical shape that is adapted to extend around the circumference of the catheter shaft 1806. The radiopaque markers 1812 may each have an outer diameter in a range of about 2.489 mm (that is, 2.489 mm±0.1 mm). The radiopaque markers 1812 may each have an inner diameter of about 2.2 mm (that is, 2.2 mm±0.01 mm) to about 2.4 mm (that is, 2.4 mm±0.01 mm). The radiopaque markers 1812 may each have a length of about 1.2 mm (that is, 1.2 mm±0.05 mm).

FIG. 21 is a view of the connection hub 1808. The connection hub 1808 may be formed of one or more polymers, such as Polycarbonate, specifically Makrolon®, which is available from Bayer Material Science of Darmstadt, Germany. The connection hub 1808 includes a bifurcate lumen, which in turn includes a main lumen 2102 and a branch lumen 2104. The branch lumen 2104 extends from the main lumen 2102 at an acute angle. The main lumen 2102 may have an inner diameter in a range of about 2.2 mm (that is, 2.2 mm±0.025 mm) to about 2.4 mm (that is, 2.4 mm±0.025 mm). The main lumen 2104 couples to a first port 2108 on a distal side of the connection hub 1808. The first port 2108 couples to the catheter shaft 1806 and the strain relief 1810. The main lumen 2104 couples to a second port 2108 on a proximal side of the connection hub 1808. The second port 2108, which may be, for example, ISO 594-1, 594-2-complaint Luer connector, is adapted to receive a guidewire and/or couple to an inflation fluid source, such as a syringe, specifically a 60 ml (cc) syringe. The branch lumen 2104 couples to a third port 2110 on the proximal side of the connection hub 1808. The third port 2110, which may be, for example, ISO 594-1, 594-2-complaint Luer connector, is adapted to receive a guidewire and/or couple to an inflation fluid source, such as a syringe, specifically a 60 ml (cc) syringe.

FIG. 22 is a view of the occlusion balloon device 1802 in a state in which the device 1802 may be provided to a medical practitioner. Specifically, the device 1802 may include a protective cover 2202 disposed about the inflatable balloon 1804. The protective cover 2202 may extend proximally beyond the proximal end of the balloon 1804 and distally beyond the distal end of the balloon 1804.

A number of variations and modifications of the disclosure can be used. It would be possible to provide for some features of the disclosure without providing others.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, for example, for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device for occluding a perforation in a superior vena cava, the device comprising:
    a catheter shaft having a first lumen and a second lumen, the first lumen being adapted to receive at least one of a guidewire and an implanted cardiac lead, and the second lumen being adapted to receive an inflation fluid, wherein the second lumen includes a cross-sectional area at a location along a length of the catheter shaft between 0.65 mm$^2$ and 1.90 mm$^2$; and
    an inflatable balloon carried by the catheter shaft and adapted to receive the inflation fluid from the second lumen, the inflatable balloon having a working length of about 65 mm to about 80 mm, and the inflatable balloon having an inflated diameter of about 20 mm to about 25 mm.

2. The device according to claim 1, wherein the inflatable balloon comprises polyurethane.

3. The device according to claim 1, wherein the inflatable balloon comprises a proximal tapered portion, a distal tapered portion, and a working portion disposed between the proximal tapered portion and the distal tapered portion, the working portion having the inflated diameter of about 20 mm to about 25 mm.

4. The device according to claim 1, wherein the first lumen and the second lumen are non-concentrically disposed within the catheter shaft.

5. The device according to claim 4, wherein the cross-sectional area of the second lumen includes a crescent shape.

6. The device according to claim 5, wherein the cross-sectional area of the second lumen is about 1 mm$^2$.

7. The device according to claim 5, wherein the crescent shape provides the cross-sectional area with a crescent-like cross-sectional shape, and wherein the crescent-like cross-sectional shape has a radius of about between 0.50 mm to 1.50 mm.

8. The device according to claim 7, wherein the radius of the crescent-like cross-sectional shape is about 1 mm.

9. The device according to claim 1, further comprising at least two radiopaque markers, wherein a first radiopaque marker is carried by the catheter shaft and a second radiopaque marker is carried by the catheter shaft.

10. The device according to claim 9, wherein the at least radiopaque markers further comprise a third radiopaque marker.

11. The device according to claim 10, wherein the inflatable balloon comprises a proximal portion, a distal portion, and an intermediate portion disposed between the proximal and distal portions, wherein the first, second, and third radiopaque markers are carried within the inflatable balloon, and wherein the first radiopaque marker is axially aligned with the proximal portion, the second radiopaque marker is axially aligned with the intermediate portion, and the third radiopaque marker is axially aligned with the distal portion.

12. The device according to claim 1, further comprising an occlusion patch detachably carried by the inflatable balloon, the occlusion patch being deployable from the inflatable balloon to occlude the perforation.

13. The device according to claim 12, wherein the occlusion patch includes at least one adhesive adapted to maintain a position of the occlusion patch within the superior vena cava.

14. The device according to claim 13, wherein the at least one adhesive is adapted to be activated by application of at least one of heat, pH, and light.

15. The device according to claim 12, wherein the occlusion patch includes a scaffold structure adapted to facilitate tissue growth therein.

16. The device according to claim 12, wherein the occlusion patch includes stem cells to facilitate bioabsorption of the occlusion patch.

17. The device according to claim 12, wherein the occlusion patch includes at least one hormonal agent adapted to promote wound healing.

\* \* \* \* \*